(12) United States Patent
Von Reden

(10) Patent No.: US 10,276,261 B2
(45) Date of Patent: Apr. 30, 2019

(54) PATIENT LIBRARY INTERFACE COMBINING COMPARISON INFORMATION WITH FEEDBACK

(71) Applicant: General Electric Company, Schenectady, NY (US)

(72) Inventor: Anna Louise Von Reden, Pittsburgh, PA (US)

(73) Assignee: General Electric Company, Schenectady, NY (US)

( * ) Notice: Subject to any disclaimer, the term of this patent is extended or adjusted under 35 U.S.C. 154(b) by 1109 days.

(21) Appl. No.: 14/554,878

(22) Filed: Nov. 26, 2014

(65) Prior Publication Data

US 2016/0147946 A1    May 26, 2016

(51) Int. Cl.
*G16H 10/60* (2018.01)
*G06F 19/00* (2018.01)

(52) U.S. Cl.
CPC ............. *G16H 10/60* (2018.01); *G06F 19/00* (2013.01)

(58) Field of Classification Search
CPC ..................... G06Q 50/22–50/24; G06F 19/30
See application file for complete search history.

(56) References Cited

U.S. PATENT DOCUMENTS

| | | | |
|---|---|---|---|
| 7,593,967 B2 * | 9/2009 | Harnsberger | G06F 17/24 |
| 2010/0191540 A1 * | 7/2010 | Esposito | G06Q 10/06 705/2 |
| 2011/0145012 A1 * | 6/2011 | Nightingale | G06F 19/3481 705/3 |
| 2012/0060216 A1 * | 3/2012 | Chaudhri | G06Q 50/22 726/21 |
| 2012/0253801 A1 * | 10/2012 | Santos-Lang | G10L 15/22 704/235 |
| 2013/0124523 A1 * | 5/2013 | Rogers | G06F 19/32 707/737 |

(Continued)

OTHER PUBLICATIONS

"CoActiv Medical Launches Exam-Jacket Pacs Viewing Enhancement." Professional Services Close-Up. Jacksonville. Nov 30, 2011. Close-Up Media, Inc. (Retrieved from https://search.proquest.com/docview/906513472?accountid=14753) (Year: 2011).*

*Primary Examiner* — Robert A Sorey
(74) *Attorney, Agent, or Firm* — Hanley, Flight and Zimmerman, LLC

(57) ABSTRACT

Disclosed and described systems, methods, and apparatus provided facilitate analysis, presentation, and comparison of clinical information. An example system includes a processor configured to provide a patient library interface. The interface displays a plurality of events along a patient timeline and a list of items for comparison to a clinical scenario. The scenario is specified in an interface configuration to trigger collection of the list of comparison items. The processor receives and adds items to the list based on a relevancy analysis of each item to the clinical scenario. The processor facilitates feedback to add, remove, and rate relevance of item(s) in the list. The processor displays item(s) from the list in conjunction with documentation from the clinical scenario and facilitates user interaction with the item(s) and documentation. The processor updates a data source based on the user feedback and user interaction.

21 Claims, 25 Drawing Sheets

(56) References Cited

U.S. PATENT DOCUMENTS

| | | | |
|---|---|---|---|
| 2013/0174073 A1* | 7/2013 | Ash | G06F 3/048 715/771 |
| 2014/0047375 A1* | 2/2014 | Koll et al. | G06F 3/0481 715/780 |
| 2014/0173464 A1* | 6/2014 | Eisenberg | H04L 65/403 715/753 |
| 2014/0343925 A1* | 11/2014 | Mankovich | G06F 17/30731 704/9 |
| 2015/0052058 A1* | 2/2015 | McCown | G06Q 50/22 705/51 |
| 2015/0149190 A1* | 5/2015 | Chace | G06F 19/00 705/2 |
| 2016/0147938 A1* | 5/2016 | McConnell | G06F 19/321 715/763 |
| 2016/0147954 A1* | 5/2016 | Ng Tari | G16H 40/20 705/3 |
| 2016/0147971 A1* | 5/2016 | Kolowitz | G06F 3/0481 715/753 |

* cited by examiner

PATIENT LIBRARY INTERFACE COMBINING COMPARISON INFORMATION WITH FEEDBACK

FIELD OF DISCLOSURE

The present disclosure relates to clinical data analysis and presentation, and more particularly to systems, methods and computer program products to facilitate identification, analysis, comparison, and presentation of clinical information.

BACKGROUND

The statements in this section merely provide background information related to the disclosure and may not constitute prior art.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example.

BRIEF SUMMARY

In view of the above, there is a need for systems, methods, and computer program products which facilitate identification, analysis, comparison, and presentation of clinical information. The above-mentioned needs are addressed by the subject matter described herein and will be understood in the following specification.

Certain examples provide a system including a processor configured to provide a patient library interface. The example patient library interface displays a plurality of events along a timeline for a patient and a list of items for comparison to a clinical scenario. The example clinical scenario is specified in a configuration of the patient library interface to trigger collection of the list of items for comparison. The example processor receives and adds items to the list of items for comparison based on a relevancy analysis of each item to the clinical scenario. The example processor facilitates user feedback to add, remove, and rate relevance of one or more items in the list of items for comparison. The example processor displays one or more items from the list of items for comparison in conjunction with documentation from the clinical scenario and facilitates user interaction with the one or more items and documentation. The example processor updates a data source based on the user feedback and user interaction.

Certain examples provide a computer-implemented method including receiving, using a processor, one or more data events determined to be relevant to a clinical scenario, the clinical scenario specified in a configuration of the patient library interface to trigger collection of the list of items for comparison. The example method includes displaying, via a patient library interface, a plurality of events along a timeline for a patient and a list of items for comparison to the clinical scenario based on the clinical scenario and the one or more data events. The example method includes receiving and adding, using the processor, items to the list of items for comparison based on a relevancy analysis of each item to the clinical scenario. The example method includes facilitating, using the processor, user feedback to add, remove, and rate relevance of one or more items in the list of items for comparison. The example method includes displaying, using the processor, one or more items from the list of items for comparison in conjunction with documentation from the clinical scenario. The example method includes facilitating, using the processor, user interaction with the one or more items and documentation. The example method includes updating, using the processor, a data source based on the user feedback and user interaction.

Certain examples provide a computer-readable storage medium including program instructions for execution by a computing device, the instructions, when executed, causing the computing device to execute a method. The example method includes receiving one or more data events determined to be relevant to a clinical scenario, the clinical scenario specified in a configuration of the patient library interface to trigger collection of the list of items for comparison. The example method includes displaying, via a patient library interface, a plurality of events along a timeline for a patient and a list of items for comparison to the clinical scenario based on the clinical scenario and the one or more data events. The example method includes receiving and adding items to the list of items for comparison based on a relevancy analysis of each item to the clinical scenario. The example method includes facilitating user feedback to add, remove, and rate relevance of one or more items in the list of items for comparison. The example method includes displaying one or more items from the list of items for comparison in conjunction with documentation from the clinical scenario. The example method includes facilitating user interaction with the one or more items and documentation. The example method includes updating a data source based on the user feedback and user interaction.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description in conjunction with the drawings in which reference numerals indicate identical or functionally similar elements.

DETAILED DESCRIPTION

Figure 1:
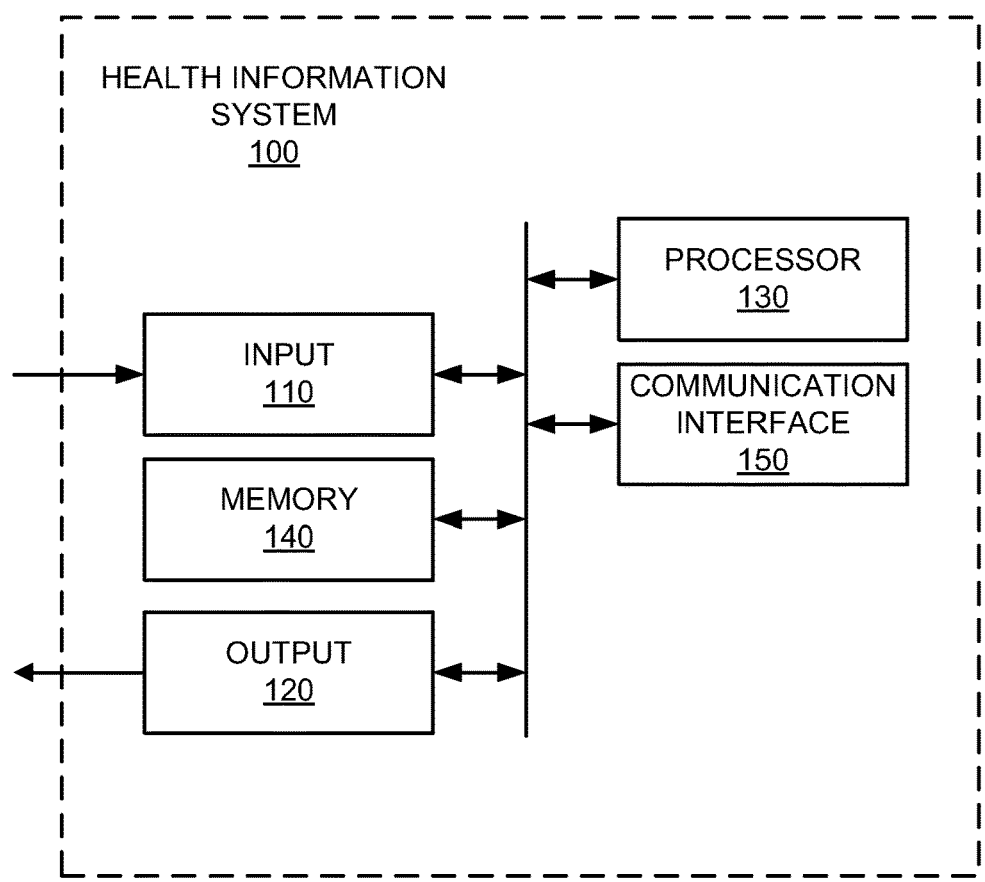
FIG. 1 shows a block diagram of an example healthcare-focused information system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. OVERVIEW

Aspects disclosed and described herein enable a patient library which combines 1) suggestions based on relevancy to a particular clinical scenarios with 2) a "build your own" pick-and-choose worklist model. A user can then trust machine suggestions and/or add his or her own content.

In certain examples, feedback is collected based on information that is displayed. A user can indicate whether displayed information is relevant and/or otherwise helpful or not. For example, clinical documentation can then be shown to a user (e.g., in a particular circumstance/clinical scenario) based on that user's opinion, peer ranking, group preference, etc. Global learning (e.g., domain wide) and/or user-specific preference can be incorporated into a relevancy analysis. Based on the makeup of displayed data, similarity of data with ontologies can be mapped. Additionally, through crowd sourcing or pooling of feedback (e.g., users in similar roles looking at similar documents), relevance/applicability data can be gathered. Rather than the data itself, how similar people use that data can be used to inform a determination of relevance, etc.

Certain examples provide a Patient Library as a visual presentation layer used with a radiologist desktop interface to identify and display relevant comparisons for an imaging study, as well as any additional clinical content that may aid in diagnoses. Additionally, the patient library provides a radiologist and/or other user with an ability to collect and organize his or her own comparisons in addition to and/or in place of system suggestions. The Patient Library relies on a relevancy algorithm to select comparison exam(s) and/or document(s) with a high likelihood of being useful to a user for a given clinical scenario (e.g., to a radiologist for a given exam he or she is reading) based upon patient clinical context including, but not limited to, a provided reason for that exam.

In certain examples, suggested comparison(s) are displayed in a section of a graphical user interface (e.g., entitled "My Comparisons", etc.), such as when a radiologist begins reading an exam. If, the relevancy algorithm's suggestions prove to be insufficient to arrive at a reasonable diagnosis, the radiologist can consult the full longitudinal list of comparison information for that patient within a "Clinical Journey" portion of the interface, and manually select his/her own comparison(s). Selecting comparison(s) adds those pieces of clinical content to the "My Comparisons" list, and this action simultaneously provides feedback to the relevancy algorithm to increase its intelligence for subsequent reads meeting similar criteria, for example.

Certain examples provide information aggregation and information filtering that cannot be accomplished in a current clinical workflow. Constantly changing large datasets dispersed across multiple systems make it difficult and time consuming to not only find important information, but also link this important information together to create a coherent patient story, for example.

Certain examples provide an intelligent recommendation system that automatically displays medical information determined to be relevant to end user(s) for a particular clinical scenario. The example intelligent recommendation system leverages natural language processing (NLP) to generate data from unstructured content; machine learning techniques to identify global usage patterns of data; and feedback mechanisms to train the system for personalized performance.

In certain examples, an apparatus responds to data source events through data source triggers and/or polling. Once data is received at the apparatus, the data is processed using available natural language processing tools to create document meta data. Document meta data is used to calculate similarity/dissimilarity of data and generate data summarization. Upon process completion, an output of natural language processing is coupled with additional data that summarizes data usage to create a robust feature set. Machine learning techniques are then applied to the feature set to determine data relevancy. Consumers can access relevant data through one or more Application Programming Interfaces (APIs).

Data processing within an example system is initiated through consumption of data events through a queuing system. A data event consumer retrieves data for relevancy algorithmic processing at processing time. An algorithm processor service applies natural language processing and machine learning techniques to determine similarity, dissimilarity, and relevancy as well as a summarization of the data. As end users access relevant data through the system, usage metrics are collected, processed, and stored through a usage rest service. Data retrieval is sourced to a data de-identification mechanism for anonymous presentation domain level data usage statistics. Relevant meta-data is stored in a database (e.g., a NoSQL data store, etc.) to enable flexible and robust analysis.

A relevancy algorithm combines aspects of domain specific knowledge with user specific knowledge and user information preference. A domain model filters global usage allowing only those points by users that are relevant to a clinical situation (e.g. only users specific to the current/selected workflow, etc.). Users are able to indicate data preference through a rating system (e.g., like/dislike, relevant/not-relevant, star rating, etc.).

Data preference and relevancy can be determined with respect to a radiology workflow and/or radiology desktop application interface, for example. An example radiology desktop provides an interaction framework in which a worklist is integrated with a diagnostic space and can be manipulated into and out of the diagnostic space to progress from a daily worklist to a particular diagnosis/diagnostic view for a patient (and back to the daily worklist). The radiology desktop shows the radiologist what is to be done and on what task(s) the radiologist is current working.

In certain examples, the radiology desktop provides a diagnostic hub and facilitates a dynamic workflow and adaptive composition of a graphical user interface. For example, the radiology desktop provides an intelligently adaptive, dynamically adjustable interface based on information, not just user clicks, as well as dynamic real time updates from a server. The radiology desktop provides a higher level framework built with multiple roles in mind (e.g., not only radiology but other -ologies as well to unify workflows and provide an expandable and reusable framework). Additionally, areas of the radiology desktop interact such that an action on one client and triggers notification of another client regarding state change(s) corresponding to the action.

In an example, one side (e.g., a left hand side) of the radiologist desktop is configurable by the radiologist. The radiologist can select a worklist on the left side of the desktop graphical user interface (GUI), and the worklist appears (e.g., "pops out" or is otherwise displayed) on the side of the radiologist desktop GUI.

Certain examples provide a radiology desktop ("Rad Desktop") that combines features for a radiologist's workflow into a single application. These features include: workload management, case selection, and access to relevant prior documentation via a patient library. A visual hierarchy supports consolidation of functionality by arranging data into compact zones that can be scanned quickly, for example.

In certain examples, the visual hierarchy of the radiology desktop supports an underlying functional framework by providing clarity to workflow elements. In certain examples, visual paradigms such as a Worklist Counter, Item Display, Clinical Journey, and My Comparisons are arranged in a very deliberate fashion. These arrangements are the product of months of design iteration, user research, and validation, for example. The visual hierarchy of the radiology desktop collects appropriate data for each element of a radiologist's workflow into a concise presentation. The radiology desktop eliminates a need for multiple applications and monitors to display non-imaging elements of the radiology workflow, for example.

Other aspects, such as those discussed in the following and others as can be appreciated by one having ordinary skill in the art upon reading the enclosed description, are also possible.

II. EXAMPLE OPERATING ENVIRONMENT

Health information, also referred to as healthcare information and/or healthcare data, relates to information generated and/or used by a healthcare entity. Health information can be information associated with health of one or more patients, for example. Health information can include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure can include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/ or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. The example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

a. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Turning now to the figures, FIG. 1 shows a block diagram of an example healthcare-focused information system 100. The example system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

As illustrated in FIG. 1, the example information system 100 includes an input 110, an output 120, a processor 130, a memory 140, and a communication interface 150. The components of the example system 100 can be integrated in one device or distributed over two or more devices.

The example input 110 can include a keyboard, a touch-screen, a mouse, a trackball, a track pad, optical barcode recognition, voice command, etc. or combination thereof used to communicate an instruction or data to the system 100. The example input 110 can include an interface between systems, between user(s) and the system 100, etc.

The example output 120 can provide a display generated by the processor 130 for visual illustration on a monitor or the like. The display can be in the form of a network interface or graphic user interface (GUI) to exchange data, instructions, or illustrations on a computing device via the communication interface 150, for example. The example output 120 can include a monitor (e.g., liquid crystal display (LCD), plasma display, cathode ray tube (CRT), etc.), light emitting diodes (LEDs), a touch-screen, a printer, a speaker, or other conventional display device or combination thereof.

The example processor 130 includes hardware and/or software configuring the hardware to execute one or more tasks and/or implement a particular system configuration. The example processor 130 processes data received at the input 110 and generates a result that can be provided to one or more of the output 120, memory 140, and communication interface 150. For example, the example processor 130 can take user annotation provided via the input 110 with respect to an image displayed via the output 120 and can generate a report associated with the image based on the annotation. As another example, the processor 130 can process updated patient information obtained via the input 110 to provide an updated patient record to an EMR via the communication interface 150.

The example memory 140 can include a relational database, an object-oriented database, a data dictionary, a clinical data repository, a data warehouse, a data mart, a vendor neutral archive, an enterprise archive, etc. The example memory 140 stores images, patient data, best practices, clinical knowledge, analytics, reports, etc. The example memory 140 can store data and/or instructions for access by the processor 130. In certain examples, the memory 140 can be accessible by an external system via the communication interface 150.

In certain examples, the memory 140 stores and controls access to encrypted information, such as patient records, encrypted update-transactions for patient medical records, including usage history, etc. In an example, medical records can be stored without using logic structures specific to medical records. In such a manner the memory 140 is not searchable. For example, a patient's data can be encrypted with a unique patient-owned key at the source of the data. The data is then uploaded to the memory 140. The memory 140 does not process or store unencrypted data thus minimizing privacy concerns. The patient's data can be downloaded and decrypted locally with the encryption key.

For example, the memory 140 can be structured according to provider, patient, patient/provider association, and document. Provider information can include, for example, an identifier, a name, and address, a public key, and one or more security categories. Patient information can include, for example, an identifier, a password hash, and an encrypted email address. Patient/provider association information can include a provider identifier, a patient identifier, an encrypted key, and one or more override security categories. Document information can include an identifier, a patient identifier, a clinic identifier, a security category, and encrypted data, for example.

The example communication interface 150 facilitates transmission of electronic data within and/or among one or more systems. Communication via the communication interface 150 can be implemented using one or more protocols. In some examples, communication via the communication interface 150 occurs according to one or more standards (e.g., Digital Imaging and Communications in Medicine (DICOM), Health Level Seven (HL7), ANSI X12N, etc.). The example communication interface 150 can be a wired interface (e.g., a data bus, a Universal Serial Bus (USB) connection, etc.) and/or a wireless interface (e.g., radio frequency, infrared, near field communication (NFC), etc.). For example, the communication interface 150 can communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

b. Example Healthcare Infrastructure

Figure 2:
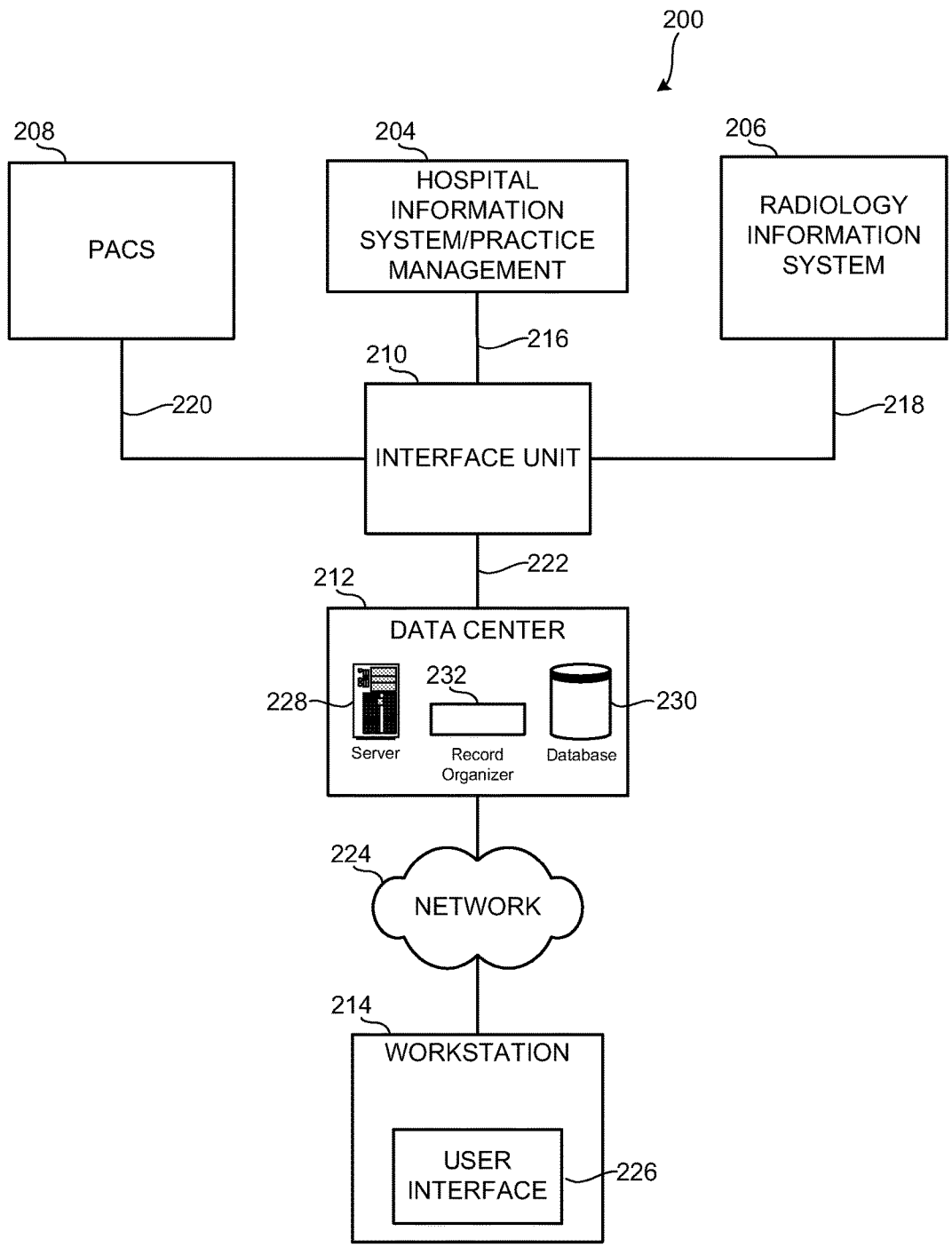
FIG. 2 shows a block diagram of an example healthcare information infrastructure including one or more systems.

FIG. 2 shows a block diagram of an example healthcare information infrastructure 200 including one or more subsystems such as the example healthcare-related information system 100 illustrated in FIG. 1. The example healthcare system 200 includes a HIS 204, a RIS 206, a PACS 208, an interface unit 210, a data center 212, and a workstation 214. In the illustrated example, the HIS 204, the RIS 206, and the PACS 208 are housed in a healthcare facility and locally archived. However, in other implementations, the HIS 204, the RIS 206, and/or the PACS 208 can be housed one or more other suitable locations. In certain implementations, one or more of the PACS 208, RIS 206, HIS 204, etc., can be implemented remotely via a thin client and/or downloadable software solution. Furthermore, one or more components of the healthcare system 200 can be combined and/or implemented together. For example, the RIS 206 and/or the PACS 208 can be integrated with the HIS 204; the PACS 208 can be integrated with the RIS 206; and/or the three example information systems 204, 206, and/or 208 can be integrated together. In other example implementations, the healthcare system 200 includes a subset of the illustrated information systems 204, 206, and/or 208. For example, the healthcare system 200 can include only one or two of the HIS 204, the RIS 206, and/or the PACS 208. Information (e.g., scheduling, test results, exam image data, observations, diagnosis, etc.) can be entered into the HIS 204, the RIS 206, and/or the PACS 208 by healthcare practitioners (e.g., radiologists, physicians, and/or technicians) and/or administrators before and/or after patient examination.

The HIS 204 stores medical information such as clinical reports, patient information, and/or administrative information received from, for example, personnel at a hospital, clinic, and/or a physician's office (e.g., an EMR, EHR, PHR, etc.). The RIS 206 stores information such as, for example, radiology reports, radiology exam image data, messages, warnings, alerts, patient scheduling information, patient demographic data, patient tracking information, and/or physician and patient status monitors. Additionally, the RIS 206 enables exam order entry (e.g., ordering an x-ray of a patient) and image and film tracking (e.g., tracking identities of one or more people that have checked out a film). In some examples, information in the RIS 206 is formatted according to the HL-7 (Health Level Seven) clinical communication protocol. In certain examples, a medical exam distributor is located in the RIS 206 to facilitate distribution of radiology exams to a radiologist workload for review and management of the exam distribution by, for example, an administrator.

The PACS 208 stores medical images (e.g., x-rays, scans, three-dimensional renderings, etc.) as, for example, digital images in a database or registry. In some examples, the medical images are stored in the PACS 208 using the Digital Imaging and Communications in Medicine (DICOM) format. Images are stored in the PACS 208 by healthcare practitioners (e.g., imaging technicians, physicians, radiologists) after a medical imaging of a patient and/or are automatically transmitted from medical imaging devices to the PACS 208 for storage. In some examples, the PACS 208 can also include a display device and/or viewing workstation to enable a healthcare practitioner or provider to communicate with the PACS 208.

The interface unit 210 includes a hospital information system interface connection 216, a radiology information system interface connection 218, a PACS interface connection 220, and a data center interface connection 222. The interface unit 210 facilitates communication among the HIS 204, the RIS 206, the PACS 208, and/or the data center 212. The interface connections 216, 218, 220, and 222 can be implemented by, for example, a Wide Area Network (WAN) such as a private network or the Internet. Accordingly, the interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with the workstation 214, via a network 224, implemented at a plurality of locations (e.g., a hospital, clinic, doctor's office, other medical office, or terminal, etc.). The network 224 is implemented by, for example, the Internet, an intranet, a private network, a wired or wireless Local Area Network, and/or a wired or wireless Wide Area Network. In some examples, the interface unit 210 also includes a broker (e.g., a Mitra Imaging's PACS Broker) to allow medical information and medical images to be transmitted together and stored together.

The interface unit 210 receives images, medical reports, administrative information, exam workload distribution information, and/or other clinical information from the information systems 204, 206, 208 via the interface connections 216, 218, 220. If necessary (e.g., when different formats of the received information are incompatible), the interface unit 210 translates or reformats (e.g., into Structured Query Language ("SQL") or standard text) the medical information, such as medical reports, to be properly stored at the data center 212. The reformatted medical information can be transmitted using a transmission protocol to enable different medical information to share common identification elements, such as a patient name or social security number. Next, the interface unit 210 transmits the medical information to the data center 212 via the data center interface connection 222. Finally, medical information is stored in the data center 212 in, for example, the DICOM format, which enables medical images and corresponding medical information to be transmitted and stored together.

The medical information is later viewable and easily retrievable at the workstation 214 (e.g., by their common identification element, such as a patient name or record number). The workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstation 214 receives commands and/or other input from a user via, for example, a keyboard, mouse, track ball, microphone, etc. The workstation 214 is capable of implementing a user interface 226 to enable a healthcare practitioner and/or administrator to interact with the healthcare system 200. For example, in response to a request from a physician, the user interface 226 presents a patient medical history. In other examples, a radiologist is able to retrieve and manage a workload of exams distributed for review to the radiologist via the user interface 226. In further examples, an administrator reviews radiologist workloads, exam allocation, and/or operational statistics associated with the distribution of exams via the user interface 226. In some examples, the administrator adjusts one or more settings or outcomes via the user interface 226.

The example data center 212 of FIG. 2 is an archive to store information such as images, data, medical reports, and/or, more generally, patient medical records. In addition, the data center 212 can also serve as a central conduit to information located at other sources such as, for example, local archives, hospital information systems/radiology information systems (e.g., the HIS 204 and/or the RIS 206), or medical imaging/storage systems (e.g., the PACS 208 and/or connected imaging modalities). That is, the data center 212 can store links or indicators (e.g., identification numbers, patient names, or record numbers) to information. In the illustrated example, the data center 212 is managed by an application server provider (ASP) and is located in a centralized location that can be accessed by a plurality of systems and facilities (e.g., hospitals, clinics, doctor's offices, other medical offices, and/or terminals). In some examples, the data center 212 can be spatially distant from the HIS 204, the RIS 206, and/or the PACS 208 (e.g., at GENERAL ELECTRIC® headquarters).

The example data center 212 of FIG. 2 includes a server 228, a database 230, and a record organizer 232. The server 228 receives, processes, and conveys information to and from the components of the healthcare system 200. The database 230 stores the medical information described herein and provides access thereto. The example record organizer 232 of FIG. 2 manages patient medical histories, for example. The record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by the system 200 via a software-as-a-service (SaaS) implementation over a cloud or other computer network, for example. In certain examples, all or part of the system 200 can also be provided via platform as a service (PaaS), infrastructure as a service (IaaS), etc. For example, the system 200 can be implemented as a cloud-delivered Mobile Computing Integration Platform as a Service. A set of consumer-facing Web-based, mobile, and/or other applications enable users to interact with the PaaS, for example.

c. Industrial Internet Examples

The Internet of things (also referred to as the "Industrial Internet") relates to an interconnection between a device that can use an Internet connection to talk with other devices on the network. Using the connection, devices can communicate to trigger events/actions (e.g., changing temperature, turning on/off, provide a status, etc.). In certain examples, machines can be merged with "big data" to improve efficiency and operations, provide improved data mining, facilitate better operation, etc.

Big data can refer to a collection of data so large and complex that it becomes difficult to process using traditional data processing tools/methods. Challenges associated with a large data set include data capture, sorting, storage, search, transfer, analysis, and visualization. A trend toward larger data sets is due at least in part to additional information derivable from analysis of a single large set of data, rather than analysis of a plurality of separate, smaller data sets. By analyzing a single large data set, correlations can be found in the data, and data quality can be evaluated.

Figure 3:
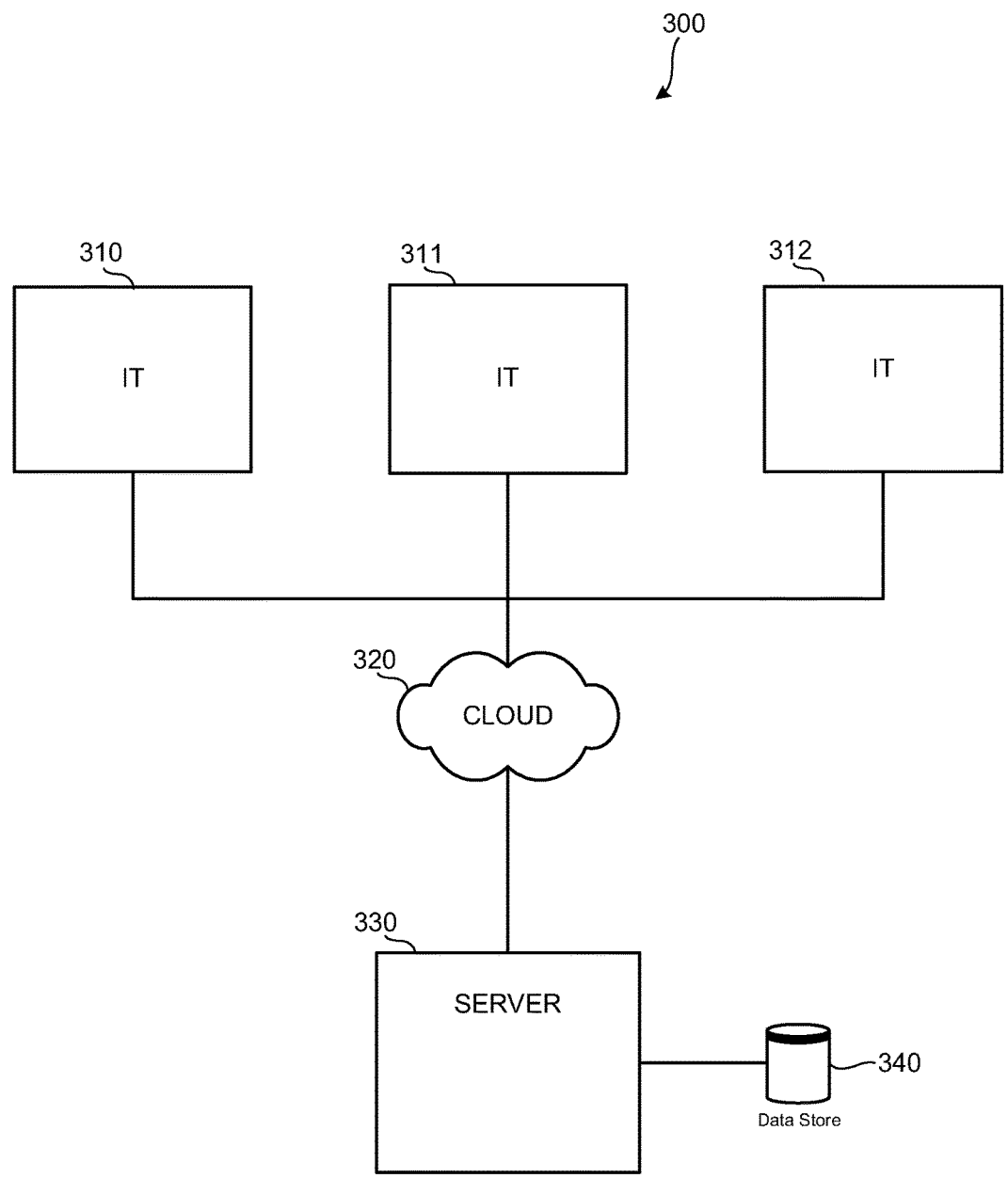
FIG. 3 shows an example industrial internet configuration including a plurality of health-focused systems.

FIG. 3 illustrates an example industrial internet configuration 300. The example configuration 300 includes a plurality of health-focused systems 310-312, such as a plurality of health information systems 100 (e.g., PACS, RIS, EMR, etc.) communicating via the industrial internet infrastructure 300. The example industrial internet 300 includes a plurality of health-related information systems 310-312 communicating via a cloud 320 with a server 330 and associated data store 340.

As shown in the example of FIG. 3, a plurality of devices (e.g., information systems, imaging modalities, etc.) 310-312 can access a cloud 320, which connects the devices 310-312 with a server 330 and associated data store 340. Information systems, for example, include communication interfaces to exchange information with server 330 and data store 340 via the cloud 320. Other devices, such as medical imaging scanners, patient monitors, etc., can be outfitted with sensors and communication interfaces to enable them to communicate with each other and with the server 330 via the cloud 320.

Thus, machines 310-312 in the system 300 become "intelligent" as a network with advanced sensors, controls, and software applications. Using such an infrastructure, advanced analytics can be provided to associated data. The analytics combines physics-based analytics, predictive algorithms, automation, and deep domain expertise. Via the cloud 320, devices 310-312 and associated people can be connected to support more intelligent design, operations, maintenance, and higher server quality and safety, for example.

Using the industrial internet infrastructure, for example, a proprietary machine data stream can be extracted from a device 310. Machine-based algorithms and data analysis are applied to the extracted data. Data visualization can be remote, centralized, etc. Data is then shared with authorized users, and any gathered and/or gleaned intelligence is fed back into the machines 310-312.

d. Data Mining Examples

Imaging informatics includes determining how to tag and index a large amount of data acquired in diagnostic imaging in a logical, structured, and machine-readable format. By structuring data logically, information can be discovered and utilized by algorithms that represent clinical pathways and decision support systems. Data mining can be used to help ensure patient safety, reduce disparity in treatment, provide clinical decision support, etc. Mining both structured and unstructured data from radiology reports, as well as actual image pixel data, can be used to tag and index both imaging reports and the associated images themselves.

e. Example Methods of Use

Clinical workflows are typically defined to include one or more steps, elements, and/or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions, elements, and/or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information. The defined clinical workflows can include manual actions, elements, and/or steps to be taken by, for example, an administrator or practitioner, electronic actions, elements, and/or steps to be taken by a system or device, and/or a combination of manual and electronic action(s), element(s), and/or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review by a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

For example, a radiology department in a hospital, clinic, or other healthcare facility facilitates a sequence of events for patient care of a plurality of patients. At registration and scheduling, a variety of information is gathered such as patient demographic, insurance information, etc. The patient can be registered for a radiology procedure, and the procedure can be scheduled on an imaging modality.

Before the patient arrives for the scheduled procedures, pre-imaging activities can be coordinated. For example, the patient can be advised on pre-procedure dietary restrictions, etc. Upon arrive, the patient is checked-in, and patient information is verified. Identification, such as a patient identification tag, etc., is issued.

Then, the patient is prepared for imaging. For example, a nurse or technologist can explain the imaging procedure, etc. For contrast media imaging, the patient is prepared with contrast media etc. The patient is guided through the imaging procedure, and image quality is verified. Using an image viewer and reporting tools, the radiologist reads the resulting image(s), performs dictation in association with the images, and approves associated reports. A billing specialist can prepare a claim for each completed procedure, and claims can be submitted to an insurer.

Such a workflow can be facilitated via an improved user desktop interface, for example.

III. EXAMPLE MEDICAL INFORMATION ANALYSIS AND RECOMMENDATION SYSTEMS

Certain examples provide an intelligent recommendation system or apparatus that automatically display medical information that is relevant to the end users for the given clinical scenario. Systems/apparatus leverage natural language processing (NLP) to generate data from unstructured content. Systems/apparatus also use machine learning techniques to identify global usage patterns of data. Systems/apparatus include feedback mechanisms to train the system for personalized performance.

Figure 4:
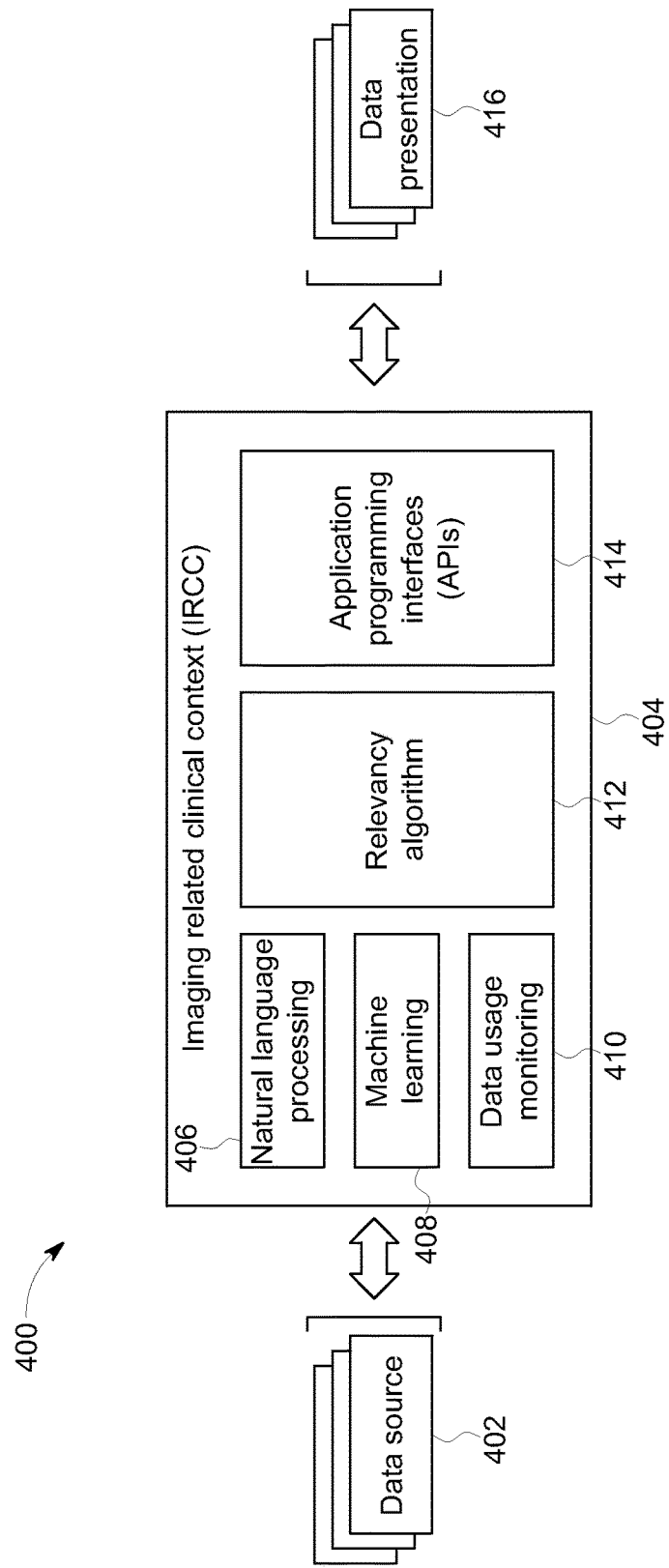
FIG. 4 illustrates an example medical information analysis and recommendation system.

FIG. 4 illustrates an example medical information analysis and recommendation system 400. The example apparatus 400 responds to data source events through data source triggers or polling. Once data is received, the received data is processed using available natural language processing tools to create document meta data. Document meta data is used to calculate similarity/dissimilarity, and data summarization. Upon process completion, 1) an output of the natural language processing is coupled with 2) additional data that summarizes data usage to create 3) a robust feature set. Machine learning techniques are then applied to the feature set to determine data relevancy. Consumers of access relevant data through one or more Application Programming Interfaces (APIs), for example.

As shown in the example of FIG. 4, the system or apparatus 400 includes one or more data source(s) 402 communicating with an imaging related clinical context (IRCC) processor 404 to provide a data presentation 416. Data source events (e.g., new documents, updated documents, lab results, exams for review, and/or other medical information, etc.) are pushed or pulled from the data source 402 to the IRCC processor 404 to trigger processing of the data from the data source. Once data is received from the data source 402 at the IRCC processor 404, the IRCC processor 404 processes the data to enrich the data and provide an indication of relevancy of the data to one or more clinical scenarios. For example, the IRCC processor 404 processes incoming data to determine whether the data is relevant to an exam for a patient being reviewed by a radiologist.

The IRCC processor 404 includes a natural language processor 406, a machine learning processor 408, and a data usage monitor 410. The processors 406, 408, 410 operate on the data from the data source 402 at the control of a relevancy algorithm 412 to process and provide input for the relevancy algorithm to analyze and determine relevance of the incoming data to a particular clinical scenario (or plurality of clinical scenarios/circumstances, etc.). Results of the relevancy algorithm's analysis of the data and its associated feature set are externalized as a presentation of data 416 via one or more application programming interfaces (APIs) 414.

For example, the natural language processor 406 parses and processes incoming data (e.g., document data) to create document meta data. The natural language processor 406 works with the relevancy algorithm 412 to calculate similarity and/or dissimilarity to a clinical scenario, concept, and/or other criterion, etc. Data is also summarized using the natural language processor 406. Once the data is processed by the natural language processor 406, an output of the natural language processing is coupled with data usage information provided by the data usage monitor's analysis of the data (e.g., whether a current user uses and/or how much, whether others use and/or how much, specific data usage, data type usage, and/or other feedback related to the data (e.g., how relevant the data is judged to be for a given clinical scenario, etc.). The combination of NLP meta data and data usage information creates a robust feature set for the incoming data from the data source 402, which can then be applied to the relevancy analysis 412. The machine learning processor 408 also applies machine learning techniques to the feature set to determine data relevancy based on the relevancy algorithm 412. The relevancy algorithm 412 outputs a resulting relevancy evaluation (e.g., a score, label, ranking, and/or other evaluation, etc.), and data presentation 416 can be generated for display, input into another program (e.g., an image viewer, reporting tool, patient library, comparison engine, etc.) via IRCC APIs 414, for example.

In the example of FIG. 4, data processing within the system 400 is initiated or triggered by consumption of one or more data events from the data source 402 by the IRCC processor 404. In certain examples, data events can be input or consumed via a queuing system, such as queuing system 500 shown in the example of FIG. 5.

The example system 500 includes a data source 502 (e.g., same as or similar to data source 402) in communication with a data source adapter 504. The data source adapter 504 receives input from a data source listener 506 which feeds a data event queue 508 and a data event consumer 510. The data source listener 506, data event queue 508, and/or data event consumer 510 can form or be viewed as a data event processor, for example.

The example system 500 further includes an algorithm request 512, an algorithm processor service 514, an IRCC rest service 516, a data rest service 518, a usage rest service 520, a data store 522 (e.g., NoSQL database, etc.), a data deidentifier 524, a data deidentification rest service 526, a data deidentification processor 528, an authenticator 530, and a graphical user interface 532 (e.g., an IRCC web user interface), for example. The algorithm request 512, algorithm processor service 514, IRCC service 516, data service 518, and/or usage rest service 520 can form or be viewed as a data relevancy processor, for example.

Figure 5:
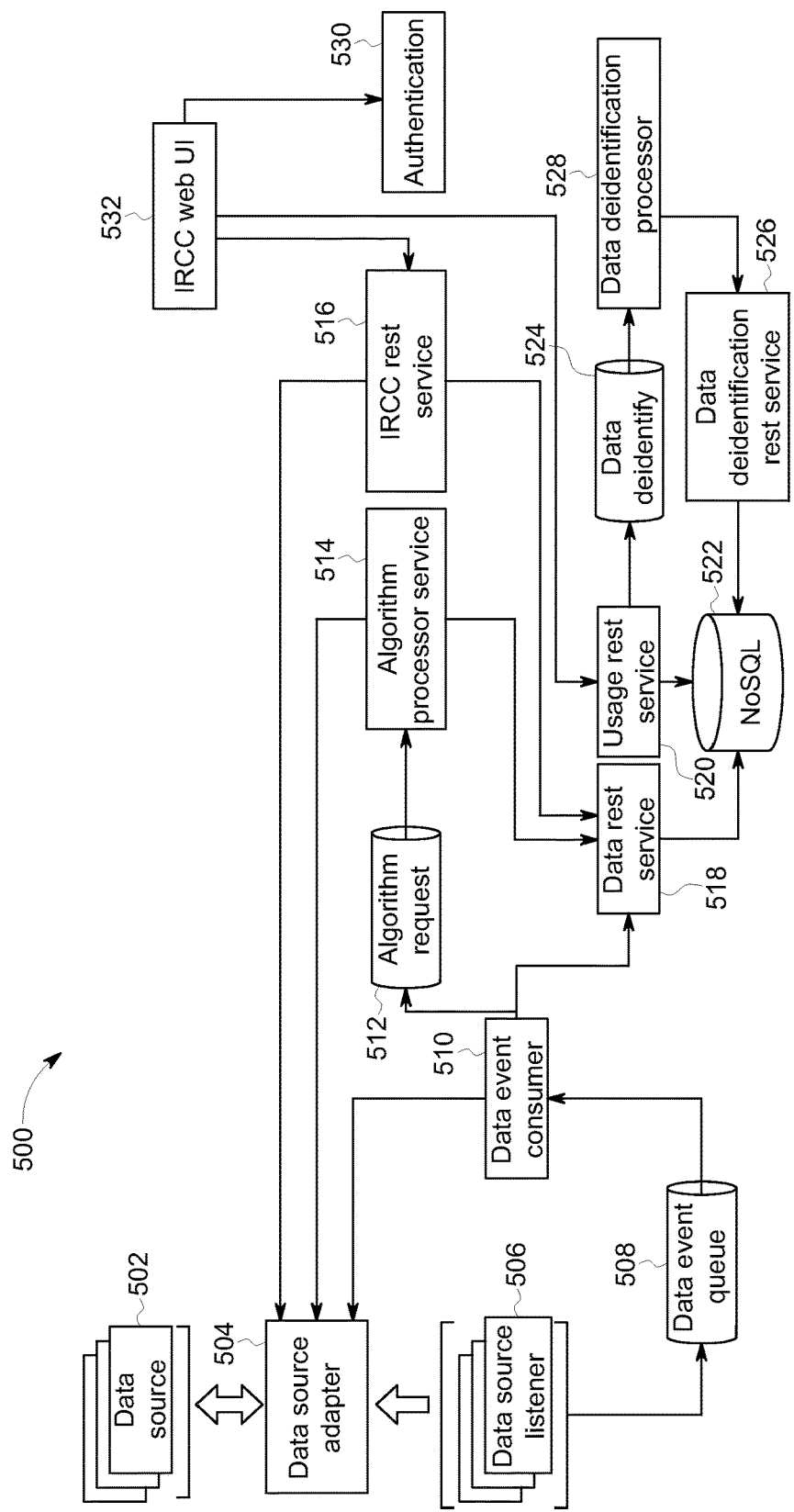
FIG. 5 illustrates an example queuing system to consume data events.

As illustrated in the example of FIG. 5, the data event consumer 510 retrieves data for relevancy algorithmic processing at processing time. The data event consumer 510 retrieves the data from the data source 520 via the data source adapter 504 which is configured to communicate with and understand one or more data source 502 to which it is connected. The data source listener 506 monitors incoming data received by the data source adapter 504 from the data source 502 and feeds the data even queue 508 when received data represents a data event (e.g., a received document, clinical data excerpt, action/result for clinical data, etc.). The data event consumer 510 consumes data events temporarily stored in the data event queue 508 and provides them based on an algorithm request 512 (e.g., data events are needed for relevancy processing). Data events are also provide by the consumer 510 to the data rest service 518 to persist data and metadata via a representational state transfer (REST) service.

The algorithm processor service 514 receives data events via the algorithm requester 512 and applies natural language processing and machine learning techniques to determine similarity, dissimilarity, and/or relevancy of the data to one or more defined criterion (e.g., a patient context, a user context, a clinical scenario, an exam, an exam type, etc.) as well as provide a summarization of the data. The algorithm processor service 514 retrieves and updates data and meta data via the algorithm requester 512.

As end users access relevant data through the system 500, usage metrics for the data are collected, processed, and stored through the usage rest service 520. Thus, as the relevancy algorithm determines that certain data is relevant to a given clinical scenario and end users 1) access and use the data, 2) do not access the data, and/or 3) access but do not use the data, the usage rest service 520 gathers and analyzes usage metrics for that data. The data 518 and its associated usage 520 can be stored in the data store 522, for example.

Data can be retrieved after being de-identified or anonymized by the data de-identification processor 528 in conjunction with the data deidentifier 524 and the data deidentification service 526. Thus, data and/or associated usage metrics can be de-identified such that an end user can benefit from relevancy without knowing the particular patient and/or user who provided the data and/or usage metric. In certain examples, based on authentication 530 of the end user, that end user may be authorized to access certain data without the data being de-identified. For example, the user may be authenticated to access his or her own data and/or usage metrics, data regarding patients under his or her care, etc. Otherwise, data deidentification occurs for anonymous presentation of domain level data usage statistics, for example. Relevant meta-data is stored in the data store 522 (e.g., a NoSQL data store) to enable flexible and robust analysis, for example.

The user interface 532 provides access to data and associated relevancy information to one or more end users, such as human users (e.g., clinicians, patients, etc.), healthcare applications (e.g., a radiology reading interface and/or other radiology desktop reporting application, etc.). A user can be authenticated 530 and provided with data, relevancy, usage, and/or other information on a push, pull, and/or other basis (e.g., push certain data based on subscription, pull other data based on user request, etc.). The services 516, 520, 526 help facilitate connection to and interaction with one or more users (e.g., human, application, system, etc.) via the interface 532, for example.

As shown in the example of FIG. 5, the IRCC service 516 can also help the data source adapter 506 communicate with the data source 502, data store 522 (via the data rest service 518), etc. The IRCC rest service 516 can retrieve similar data and/or metadata for provision via the interface 532, for example.

In certain examples, data, usage, and/or relevancy can continue to update and/or otherwise evolve through passage of time, changing circumstances, additional clinical scenarios, etc. In certain examples, the user interface 352 may indicate when updated information becomes available.

Figure 6:
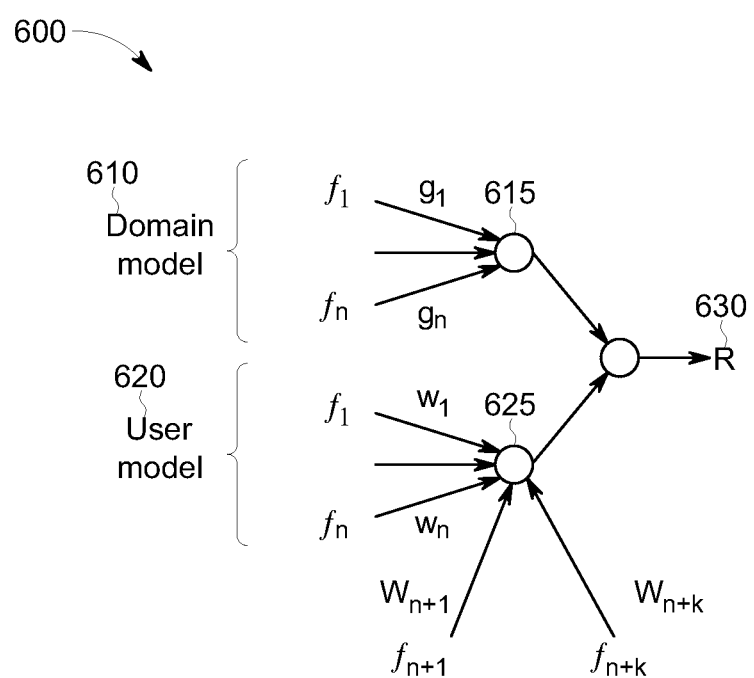
FIG. 6 illustrates an example relevancy algorithm.

FIG. 6 illustrates an example data relevancy algorithm 600. The example algorithm 600 can be employed by the relevancy algorithm 412, algorithm processor service 514, and/or other relevancy calculator. The example relevancy algorithm of FIG. 6 combines aspects of domain specific knowledge with user specific knowledge and user information preference to determine relevancy of certain provided data to certain criterion (e.g., clinical scenario, clinician, patient, exam, condition, etc.). The example relevancy algorithm 600 includes a domain model 610 and a user model 620. The domain model 610 filters (e.g., $f_1 \ldots f_n$) global usage (e.g., $g_1 \ldots g_n$) to identify a subset 615 of global usage. The user model 620 filters users to allow only those points 625 by users relevant to the clinical situation (e.g., $f_1 \ldots f_{n+k}$) only users specific to a given workflow (e.g., $w_1 \ldots w_{n+k}$). Users are able to indicate data preference through a rating system (e.g., like/dislike, relevant/not-relevant, star rating, etc.). Results 615, 625 of the domain model 610 and user model 620 are combined into a result set R 630 indicating a relevancy of the data to the situation.

Thus, certain examples facilitate information aggregation and information filtering beyond what previously existed within a clinical workflow. Constantly changing large datasets dispersed across multiple systems make it difficult and time consuming to not only find important information, but also link this information together to create a coherent patient story. The systems and methods of FIGS. 4-6 help to remedy these deficiencies and provide relevant data to enhance clinical review, diagnosis, and treatment, for example.

The event-based architecture of systems 400, 500 provides more efficient data processing, and natural language processing creates an easy to understand information hierarchy. The adaptable systems 400, 500 and algorithm 600 are able to respond in a variety of clinical environments. Faster display of information also leads to a more efficient workflow.

For example, the systems 400, 500 can be configured to provide a radiology encounter data display and apply heuristics to radiology data to determine relevancy to a current exam for review. Systems 400, 500 provide intelligent presentation of clinical documents in conjunction with results of the relevancy analysis. In certain examples, natural language processing is applied to clinical observational data, and resulting meta data is analyzed for an adaptive, complex relevancy determination. Adaptive and (machine) learned relevancy of clinical documents and data can then be provided. In certain examples, contextual understanding is provided for a given -ology (e.g., radiology, cardiology, oncology, pathology, etc.) to provide diagnostic decision support in context.

In certain examples, data analysis is coupled with data display to provide a hierarchical display of prior imaging and/or other clinical data. Contextual diagnostic decision support helps to facilitate improved diagnosis in radiology and/or other healthcare areas (-ologies). Knowledge engineering is applied to clinical data to generate NLP, data mining, and machine learning of radiology reports and other clinical to provide an indication of relevancy of that report/data to a given exam, imaging study, etc. Systems 400, 500 adapt and learn (e.g., machine learning) to build precision in relevancy analysis.

Figure 7:
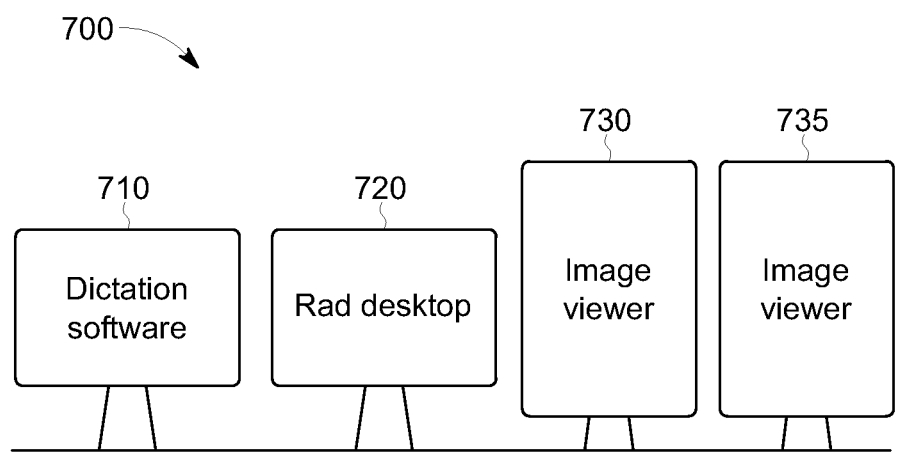
FIG. 7 shows an example image viewer and analysis system.

For example, the relevancy analysis systems and methods can be applied in the image reviewing and reporting context. In certain examples, exam imaging can be handled by a separate viewer application while dictation and report management is provided by another application. As shown in the example of FIG. 7, an image viewer is implemented on a plurality of diagnostic monitors 730, 735. A dictation application 710 either sits side-by-side with a radiology desktop 720, on a same monitor as the radiology desktop 720, or behind/in front of the radiology desktop 720 such that a user toggles between two windows 710, 720. In other examples, image viewing, image analysis, and/or dictation can be combined on a single workstation.

A radiologist, for example, can be presented with summary information, trending, and extracted features made available so that the radiology does not have to search through a patient's prior radiology report history. The radiologist receives decision support including relevant clinical and diagnostic information to assist in a more definitive, efficient diagnosis.

In certain examples, a current study for one or more patients X, Y, Z is prefetched from a data source 402, 502. If a current study for patient X is being processed, prior report(s) for patient X are located (e.g., from a picture archiving and communication system (PACS), enterprise archive (EA), radiology information system (RIS), electronic medical record (EMR), etc.). For example, report text and prior study metadata including a reason for exam, exam code, study, name, location, etc., are provided from a PACS as prior data for mining, extraction, and processing.

A report summary, similarity score ($s_{index}$) for each document, a summary tag for a timeline display, and select quantitative data extracts, etc., can be provided as a result of the mining, extraction, and processing of prior document data for the patient. Additionally, a value of a feature ($v_{feat}$) from a feature set provided as a result of the mining, extraction, and analysis can be determined based on one or more of modality, body part, date, referring physician, etc. Then, using $v_{feat}$ and $s_{index}$, a relevancy score can be calculated using, for example:

$$\text{Relevancy} = f(s_{index}, v_{feat}) \qquad (\text{Eq. 1}).$$

Thus, relevancy is a function of an identified feature and a similarity score for identified data in comparison to a current exam, study, patient, etc.

In certain examples, a workload manager resides on a side (e.g., a left-hand side, a right-hand side, top, bottom, etc.) of a radiology desktop and can be opened or otherwise accessed to access exams. When an exam access is not desired, the workload manager can be closed or hidden with respect to the radiology desktop (e.g., with respect to a diagnostic hub on the radiology desktop). The workload manager and/or an associated diagnostic hub can leverage the information identification, retrieval, and relevancy determination systems and methods disclosed and described herein to provide information for research, comparison, supplementation, guidance, etc., in conjunction with an exam under review (e.g., via an exam preview panel from a patient library, etc.).

For example, the diagnostic hub can include a patient banner. The patient banner displays patient demographic data as well as other patient information that is persistent and true regardless of the specific exam (e.g., age, medical record number (MRN), cumulative radiation dose, etc.). The diagnostic hub also includes a primary exam preview panel. The primary exam preview panel provides a summary of the exam that the radiologist is currently responsible for reading (e.g., the exam that was selected from an active worklist). Exam description and reason for exam can be displayed to identify the exam, followed by metadata such as exam time, location, referrer, technologist, etc.

A patient library is devoted to helping a radiologist focus on relevant comparison exams, as well as any additional clinical content to aid in diagnosis. The patient library of the diagnostic hub can include subsections such as a clinical journey, comparison list, a comparison exam preview panel, etc. The clinical journey is a full patient 'timeline' of imaging exams, as well as other clinical data such as surgical and pathology reports, labs, medications, etc. The longitudinal view of the clinical journey helps the radiologist notice broader clinical patterns more quickly, as well as understand a patient's broader context that may not be immediately evident in a provided reason for the primary exam. Tools can be provided to navigate within the clinical journey. A user can adjust a time frame, filter for specific criteria, turn relevancy on or off, add or remove content categories, etc. The clinical journey also integrates with the comparison list. Modifying filter or search criteria in the clinical journey can impact the exams displayed on the comparison list.

The comparison list provides one or more available comparison exams for the current patient/primary exam. The comparison list provides a quick access point for selecting comparisons, as opposed to the more longitudinal clinical journey. Display can be limited to only show relevant exams based on the relevancy algorithm, for example. The comparison exam preview panel is similar to the primary exam preview panel, with alterations in content display to account for a radiologist's shift in priorities when looking at a comparison (e.g., selected from the comparison list, etc.). Rather than providing a reason for exam, a history and impression from the exam's report are displayed (or the whole report, if extraction is not possible or desired, etc.). The comparison previous pane also generates and/or provides a relevancy score (e.g., 0-100%) from the relevancy algorithm 600 and associated systems 400, 500 based on body part, modality, exam time, and/or other variable(s).

Thus, the diagnostic hub works with a processor, a relevancy engine, and a knowledge manager to filter and/or other process data (e.g., study data, image data, clinical data, etc.) for mining and extraction (e.g., of text), extraction (e.g., pixel data), and evaluate, via the relevancy engine, a relevance of the data to a particular exam, study, patient, etc. The knowledge manager organizes and stores relevance information for later retrieval and application in response to query and/or observer, for example.

Figure 8:
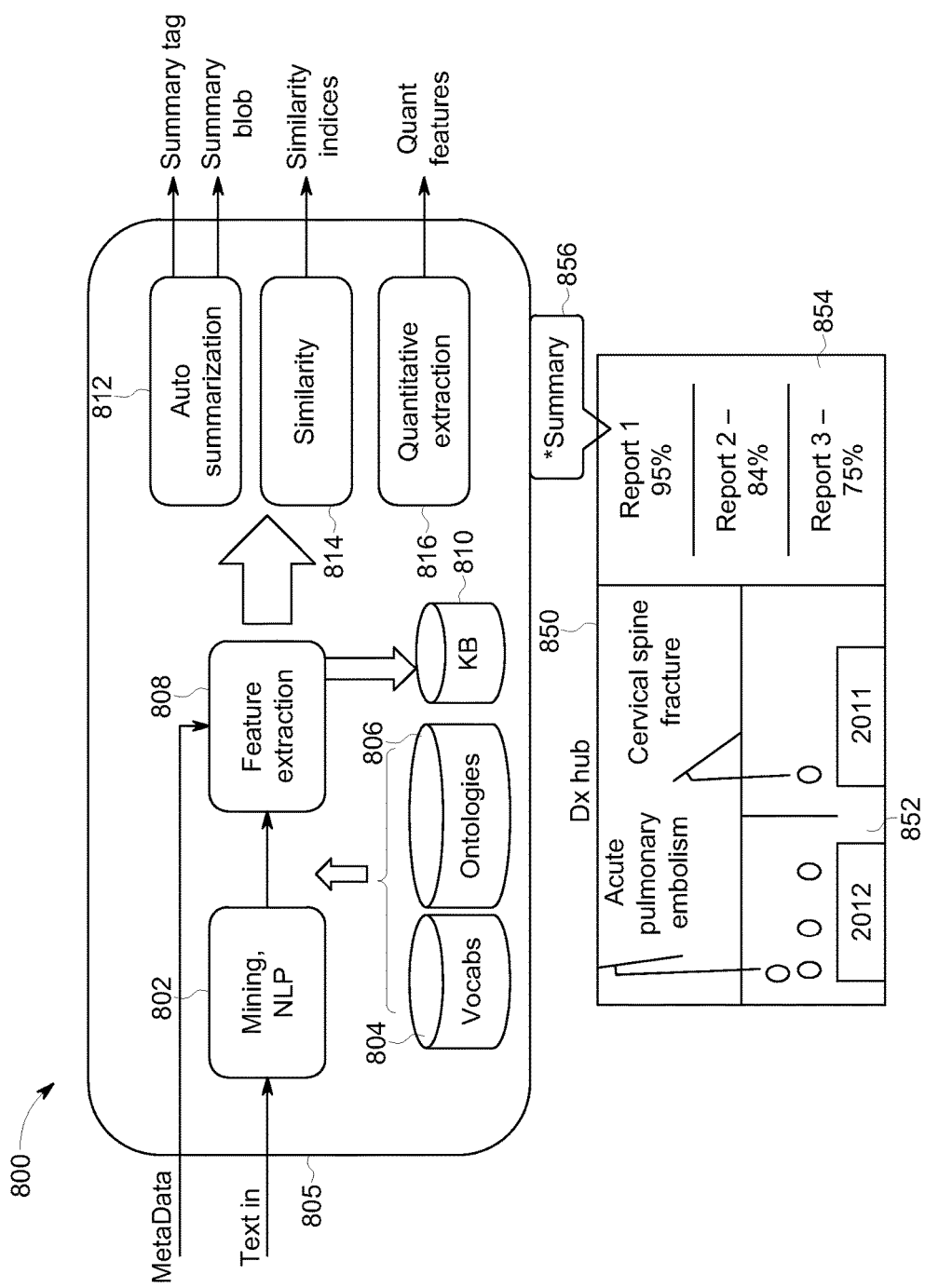
FIG. 8 illustrates an example data processing system including a processing engine and a diagnostic hub.

FIG. 8 illustrates an example data processing system 800 including a processing engine 805 and a diagnostic hub 850. The processing engine 805 processes input text documents and metadata by data mining and applying NLP techniques 802 to process the data based on one or more vocabularies 804, ontologies 806, etc. NLP output is provided for feature extraction 808. The feature extractor 808 provides feature information to a knowledge base 810 for storage, as well as for further processing.

One or more analyses are applied to the extracted features such as auto summarization 812, similarity 814, quantitative extraction 816, etc. Auto summarization 812 generates a summary tag, summary blog, etc., from one or more extracted features. Similarity 814 generates one or more similarity indices based on comparison of feature information. Quantitative extraction 816 processes extracted features and provides quantitative features. Resulting summary, similarity, and quantitative information can be stored in local and/or cloud-based document storage.

As shown in the example of FIG. 8, the diagnostic hub 850 formulates and displays reporting information based on the features and associated information provided by the processor 805. Information provided via the diagnostic hub 850 includes trending and timeline information 852, and one or more reports 854. Upon selection of (e.g., clicking on, mouse over, etc.) a report, a summary 856 of that report can be provided, for example.

Figure 9:
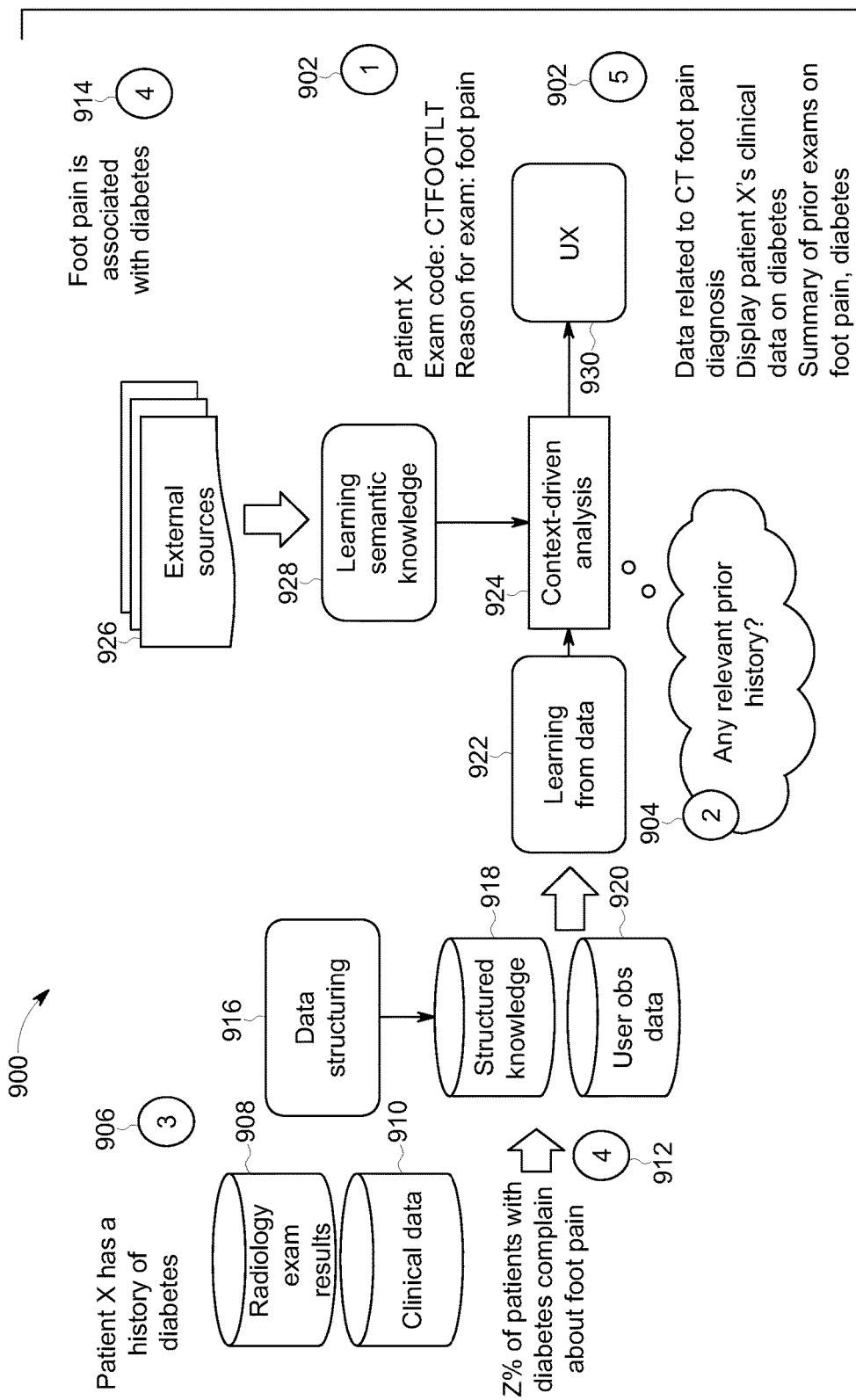
FIG. 9 shows an example context-driven analysis using an image-related clinical context relevancy algorithm.

FIG. 9 shows an example context-driven analysis 900 using an image-related clinical context relevancy algorithm. At 902, an exam is retrieved for review. For example, a patient identifier (e.g., Patient X, etc.), an exam code (e.g., CTFOOTLT, etc.), and a reason for exam (e.g., foot pain, etc.) are provided. At 904, relevant prior history for that patient, exam, reason, etc., is identified. At 906, identified relevant history information is retrieved. For example, Patient X, who has come in for an exam including a left foot CT image due to foot pain, may have a history of diabetes. History information can come from a variety of sources such as radiology exam results 908, clinical data 910, etc. At 912 and 914, additional clinical information can be provided with the patient history information. For example, a certain percentage of patients with diabetes complain about foot pain; foot pain is associated with diabetes; etc.

Since the historical and other clinical data can come in a variety of formats, retrieved data is structured 916 to provide structured knowledge 918. User observation data 920 can also be added to supplement the structured knowledge 918.

The combined data 918, 920 is then analyzed to learn from that data 922. Learning (e.g., machine learning, etc.) from the data can drive a context-driven analysis 924.

In addition to patient historical information, user observations, etc., data from external source(s) 926 can be used to drive learning semantic knowledge 928. Semantic knowledge 928 can then be used with the learning from data 922 to perform context-driven analysis 924 (e.g., including a relevancy evaluation, supplemental information, best practices, workflow, etc.).

Results of the analysis 924 are provided via a user interface 930 to a user such as a clinician, other healthcare practitioner, healthcare application (e.g., image viewer, reporting tool, archive, data storage, etc.). For example, data related to CT foot pain diagnosis; a display of Patient X's clinical data on diabetes; a summary of prior exams on foot pain, diabetes, etc.; etc., can be provided via the interface 930.

IV. EXAMPLE INTERACTION FRAMEWORK METHODS

Figure 10:
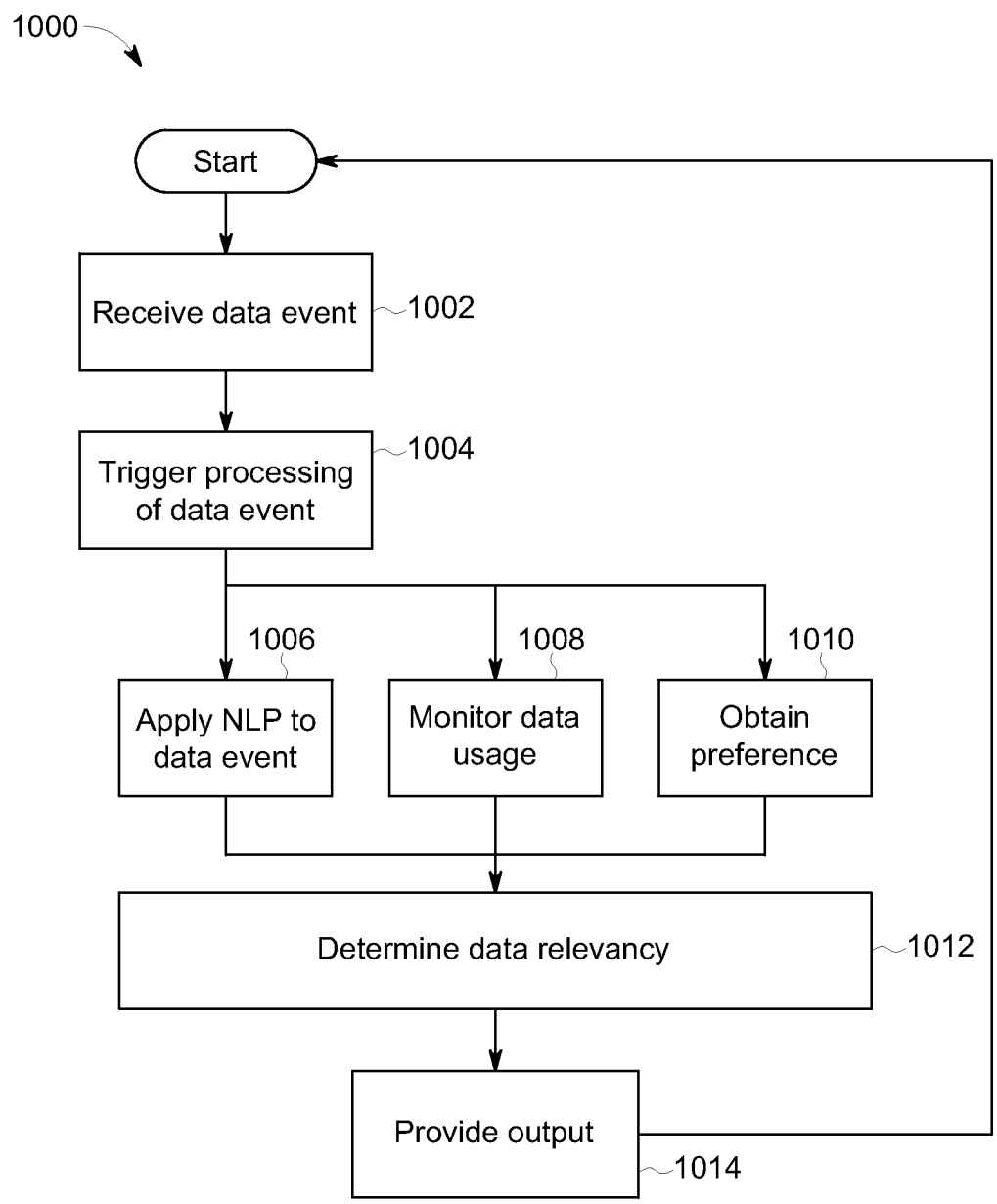
FIG. 10 illustrates a flow diagram for an example method to evaluate medical information to provide relevancy and context for a given clinical scenario.

Flowcharts representative of example machine readable instructions for implementing and/or executing in conjunction with the example systems, algorithms, and interfaces of FIGS. 1-9 are shown in FIG. 10. In these examples, the machine readable instructions comprise a program for execution by a processor such as the processor 2012 shown in the example processor platform 2000 discussed below in connection with FIG. 20. The program can be embodied in software stored on a tangible computer readable storage medium such as a CD-ROM, a floppy disk, a hard drive, a digital versatile disk (DVD), a BLU-RAY™ disk, or a memory associated with the processor 2012, but the entire program and/or parts thereof could alternatively be executed by a device other than the processor 2012 and/or embodied in firmware or dedicated hardware. Further, although the example program is described with reference to the flowchart illustrated in FIG. 10, many other methods of implementing the examples disclosed and described here can alternatively be used. For example, the order of execution of the blocks can be changed, and/or some of the blocks described can be changed, eliminated, or combined.

As mentioned above, the example processes of FIG. 10 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 10 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 10 illustrates a flow diagram for an example method 1000 to evaluate medical information to provide relevancy and context for a given clinical scenario. At block 1002, a data event is received at a processor. The data event can be pushed and/or pulled from a data source to the data processor (e.g., an IRCC processor such as IRCC processor 404, data event consumer 510, etc.). At block 1004, receipt of the data event triggers processing of the data event by the processor. For example, when the data source listener 506 detects receipt of a data event from the data source 502, the listener 506 provides the data event in a queue 608 which triggers the data event consumer 510 to process the data event.

At block 1006, natural language processing is applied to the data event. For example, document data provided from a data source is processed using NLP techniques to generate structured data from the data event. At block 1008, the structured data is used to learn and determine similarity/dissimilarity and relevancy of the data to the given clinical scenario. For example, natural language processing and machine learning (e.g., by the machine, system, or processor) leverages prior patterns, history, habits, best practices, particular data, etc., to analyze similarity and/or dissimilarity of the data and relevance to the given clinical scenario as well as improve operation and interpretation for future analysis.

At block 1008, data usage is also monitored to provide usage information for the data. For example, how frequently, how recently, how effectively, etc., user(s) (e.g., a current user, peer users, etc.) use the data being processed can be monitored and tabulated to form data usage statistics at a particular level (e.g., at a domain level, group level, individual level, etc.).

At block 1010, user preference information can be obtained to factor into data analysis. For example, users can indicate a preference for data through a rating system (e.g., like/like, relevant/irrelevant, thumbs up/thumbs down, stars, numerical rating, etc.).

At block 1012, data analysis, usage information, and/or preference information is provided to a relevancy algorithm to determine relevance of the data associated with the data event to the given clinical scenario. For example, domain and user usage, knowledge, preference, and workflow filters are applied to the gathered analysis and information to provide an indication (e.g., a score, a category, a range, a classification, etc.) of relevancy to the given clinical scenario (e.g., a foot x-ray, an abdominal ultrasound, dizziness, etc.).

At block 1014, an output is made available via an interface. For example, an output is made available to one or more external users (e.g., human, application, and/or system users, etc.) via an API, a graphical user interface, etc. Thus, in an example, document(s) associated with the data event along with analysis, contextual information, and a relevancy score can be provided via the interface.

Thus, information can be identified, retrieved, processed, and provided to help enrich and enlighten examination, diagnosis, and treatment of a patient in a collaborative, expansive, and evolutionary (e.g., learning) system. For example, a graphical user interface can be configured to dynamically accommodate both a diagnostic hub and workload manager and facilitate workload management as well as communication and collaboration among healthcare practitioners.

V. EXAMPLE RADIOLOGY DESKTOP INTERFACE SYSTEMS

Certain examples provide a radiology desktop interface which combines workload management tools with a new, patient-centric exam reading space (referred to herein as a "Diagnostic Hub"). Exam data for one or more patients can be displayed via the diagnostic hub, which provides support for a radiologist's workflow.

Figure 11:
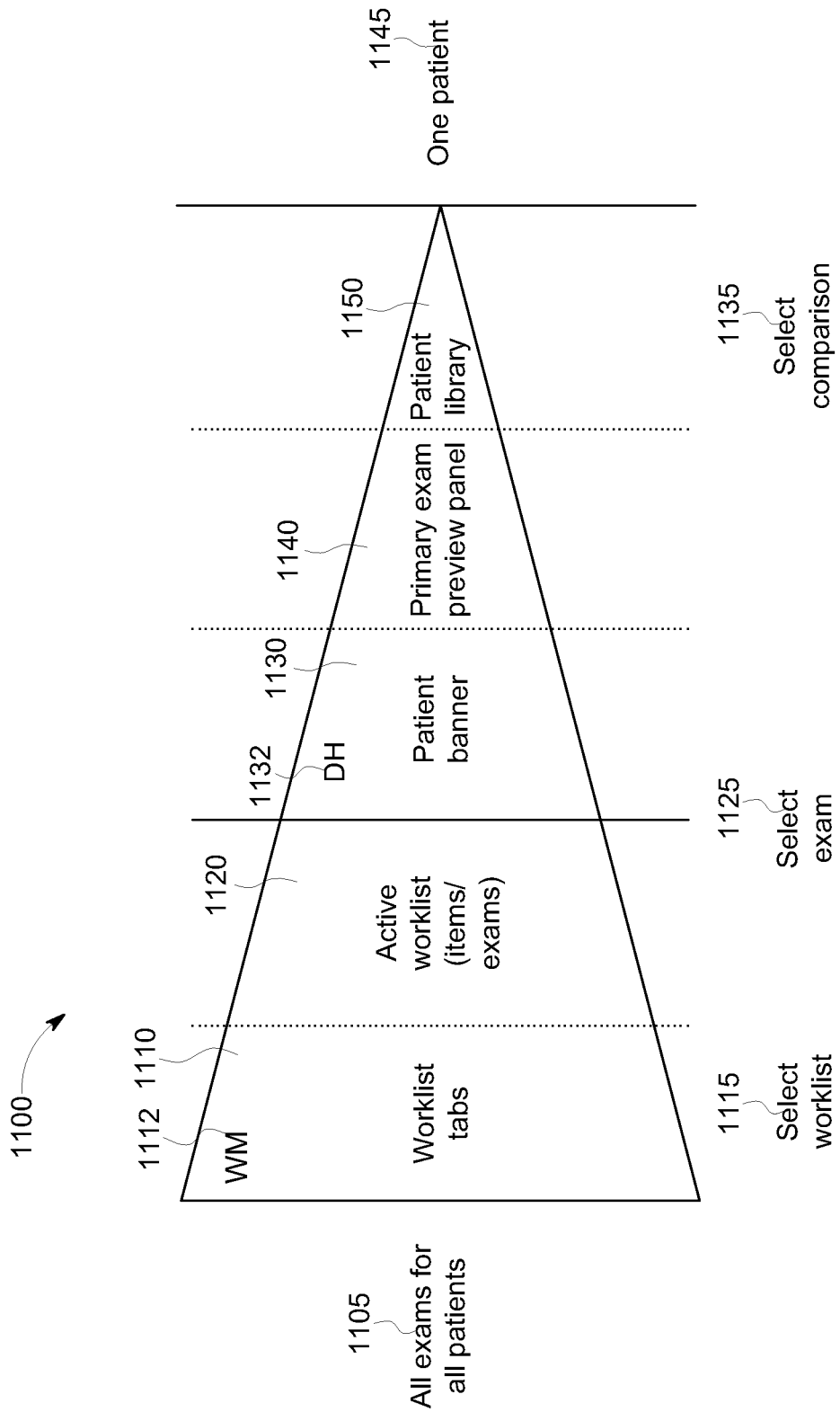
FIG. 11 illustrates an example of a left-to-right drill-down model.

Radiology desktop is design to support the radiologist workflow from a bird's eye view or overview of available unread exams to a nuts and bolts or detail view of a detailed clinical context for a single patient. FIG. 11 illustrates an example of a left-to-right drill-down model 1100. The model flow 1100 provides a framework for wayfinding as users move from macro to micro and back again. The model 1100 continuously orients users in their current tasks.

As shown in the example of FIG. 11, exams for patients in a collection of patients (e.g., patients associated with a physician, patients in a department, patients in a hospital, etc.) 1105 are provided to a workload manager 1112 including worklist tabs 1110. A worklist is selected 1115 and an active worklist 1120 is provided via the workload manager 1112. The active worklist 1120 displayed via the workload manager 1112 includes exams and other items for the selected worklist. An exam can be selected 1125 from the active worklist 1120.

The selected exam 1125 is provided via a diagnostic hub 1132. The diagnostic hub 1132 provides a patient banner 1130 in conjunction with the selected exam 1125. A primary exam preview panel 1140 can be selected from the patient banner 1130. Via the primary exam preview panel 1140, a patient library 1150 can be accessed. Using the patient library 1150, a patient 1145 can be selected for comparison 1135.

In certain examples, exam imaging can be handled by a separate viewer application while dictation and report management is provided by another application. As shown in the example of FIG. 7, an image viewer is implemented on a plurality of diagnostic monitors 730, 735. A dictation application 710 either sits side-by-side with a radiology desktop 20, on a same monitor as the radiology desktop 720, or behind/in front of the radiology desktop 720 such that a user toggles between two windows 710, 720. In other examples, image viewing, image analysis, and/or dictation can be combined on a single workstation.

In certain examples, a workload manager resides on a side (e.g., a left-hand side, a right-hand side, top, bottom, etc.) of a radiology desktop and can be opened or otherwise accessed to access exams. When an exam access is not desired, the workload manager can be closed or hidden with respect to the radiology desktop (e.g., with respect to a diagnostic hub on the radiology desktop).

Figure 12A:
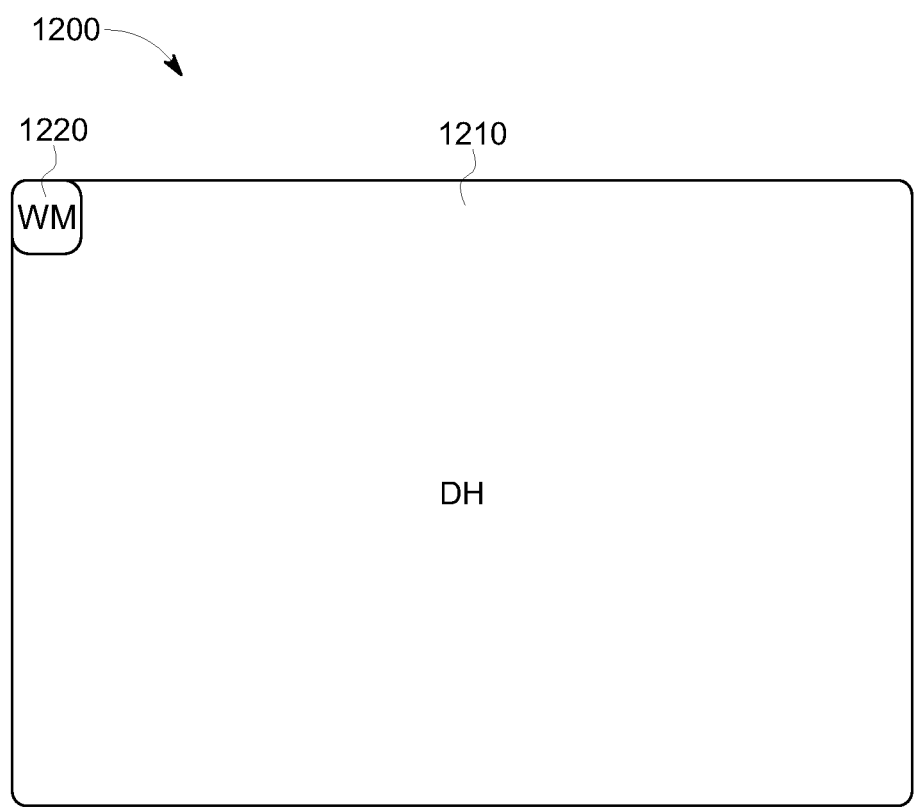
FIGS. 12A-12D illustrate a sequence or evolution of display configuration.
Figure 12B:
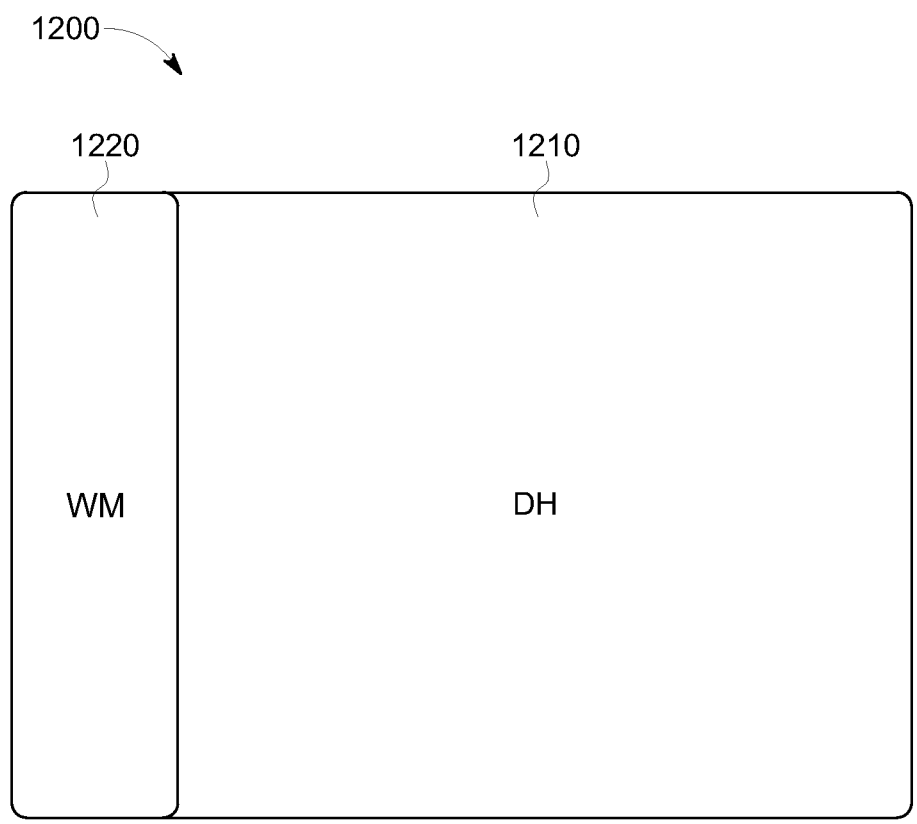

FIGS. 12A-12D illustrate a sequence or evolution of display configuration. As shown in the example of FIG. 12A, a diagnostic hub 1210 occupies a majority of available display area on a display 1200, and a workload manager 1220 is represented in miniaturized or icon form. The workload manager 1220 can be minimized where a worklist is not being used. As illustrated in the example of FIG. 12B, the workload manager 1220 can be expanded, such as by user selection, dragging, clicking, etc. In a two-column, collapsed tab state such as that shown in FIG. 12B, limited, high priority content such as patient name, identifier (ID), modality, urgency, etc., can be shown via the workload manager 1220.

Figure 12C:
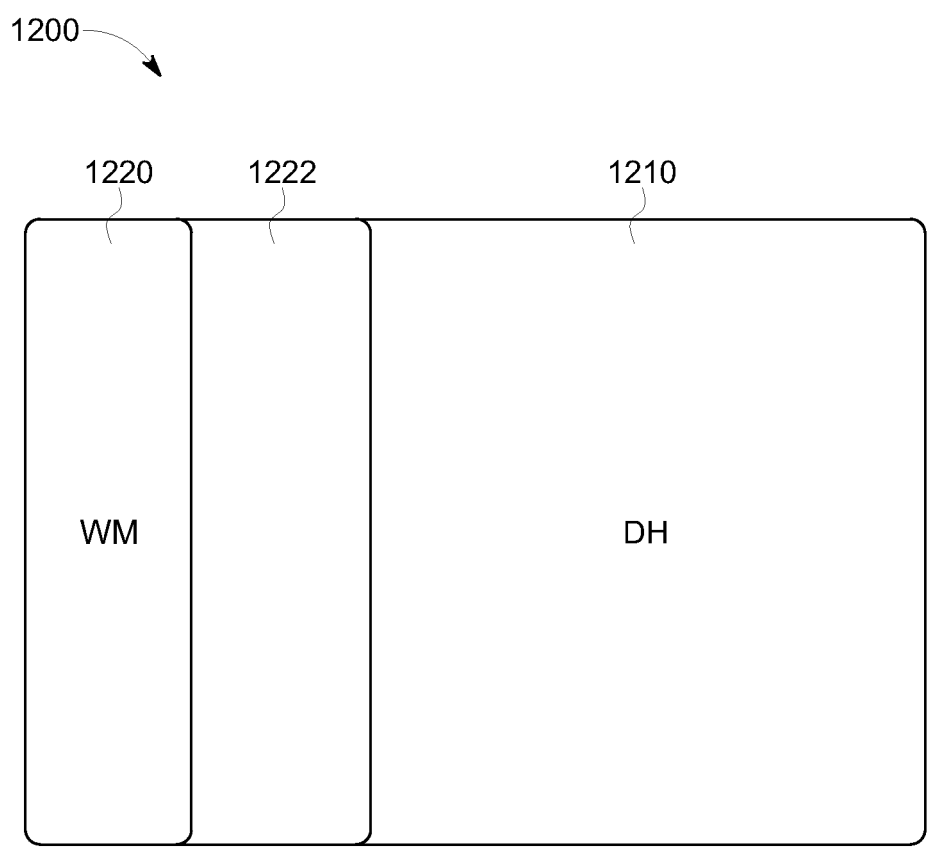

The example of FIG. 12C depicts an interface 1200 in a three-column display state. In the example of FIG. 12C, the diagnostic hub 12210 is shown in conjunction with a two-column workload manager 1220, 1222. The interface 1200 of FIG. 12C provides a flexible user interface that responds to user selection. Content thresholds can be set to reveal appropriate levels of information depending on column 1210, 1220, 1222 width.

Figure 12D:
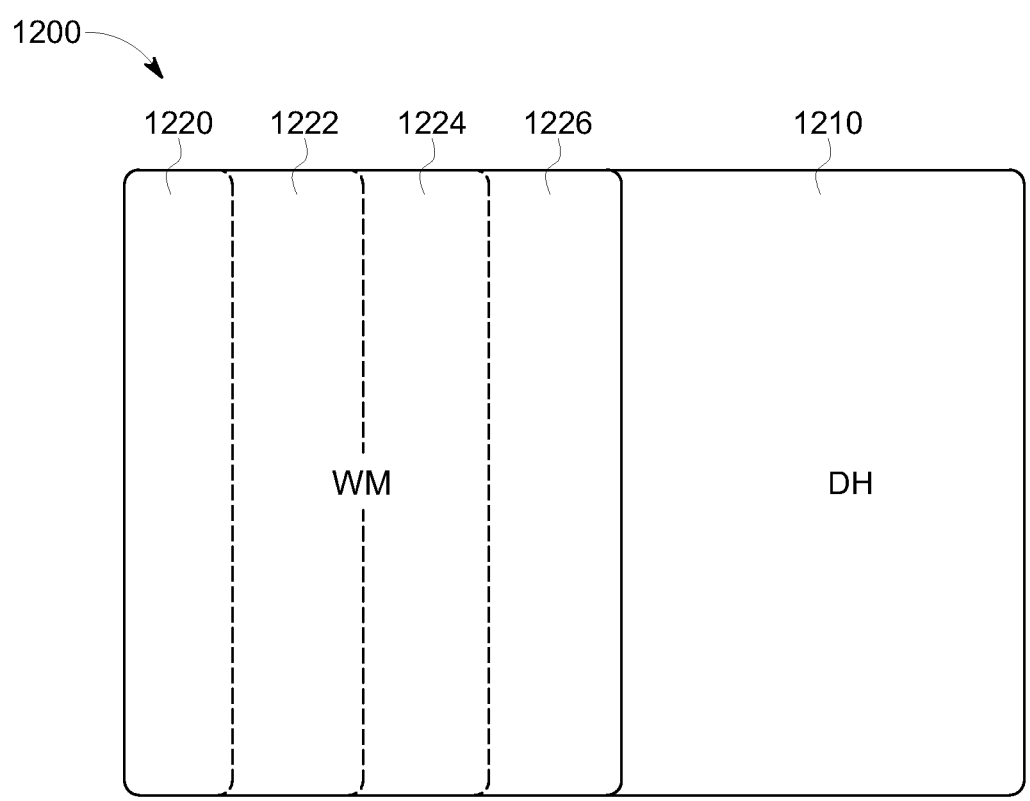

FIG. 12D provides another example in which the workload manager is divided according to a gradient into multiple columns 1220, 1222, 1224, 1226 in conjunction with the diagnostic hub 1210. The example interface 1200 of FIG. 12D also provides a flexible user interface that responds to user selection. Content thresholds can be set to reveal appropriate levels of information depending on column 1210, 1220, 1222, 1224, 1226 width.

Figure 13:
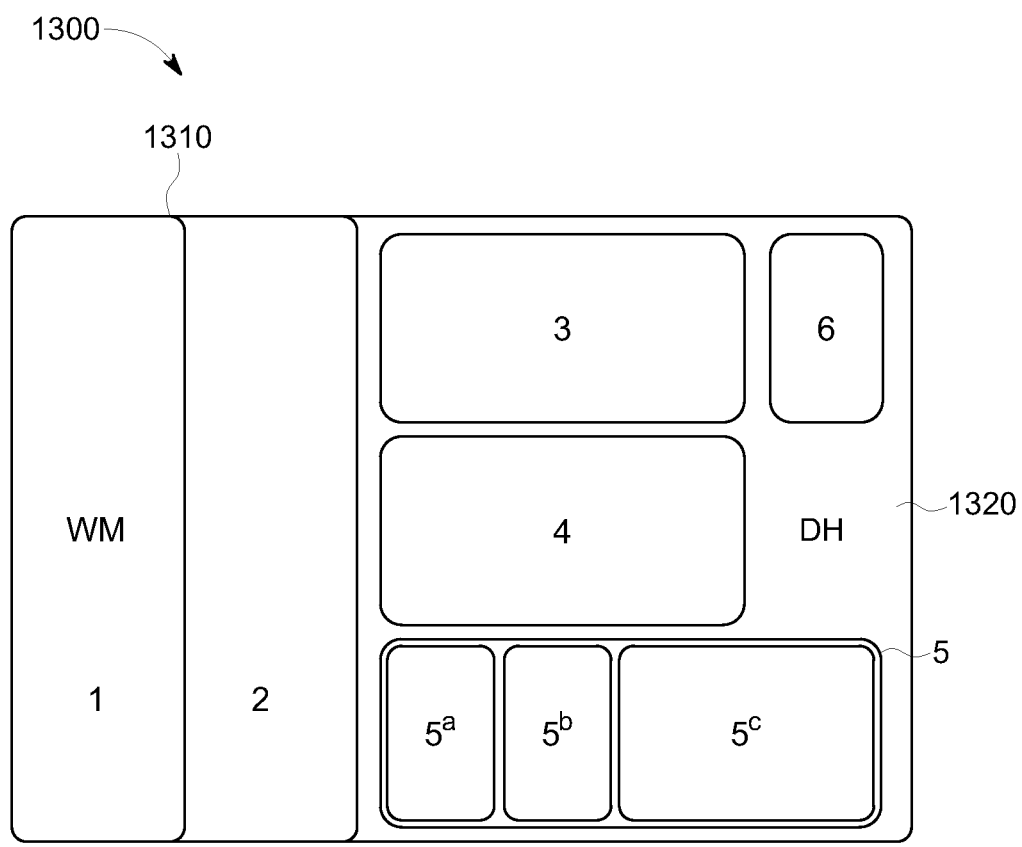
FIG. 13 illustrates an example radiology interface including a workload manager and a diagnostic hub.

FIG. 13 illustrates an example radiology interface 1300 including a workload manager 1310 and a diagnostic hub 1320. The workload manager 1310 shown in the example interface 1300 includes a plurality of workload manager columns 1, 2. A first column 1 includes worklist tabs providing access to various tasks that a radiologist may address during a shift. A first category, 'My Work', houses various worklists from which a radiologist may choose to work. My Work can be divided into two subcategories: 1) items, potentially from any worklist, that a radiologist has actively reserved, been assigned by others to or begun reading ('Reserved,' 'Assigned', 'Saved Drafts', etc.), and 2) saved worklists that may be collaborative, cross-departmental, rotation-specific, and/or otherwise customized, for example. Other categories include 'Saved Cases', for cases that a radiologist wants to reference later, 'Messages' for communication and collaboration, 'My History' for easy access recently finalized exams, and 'Protocols' for scheduled or ordered exams that may involve consultation with a radiologist on proper exam performance, for example.

A second column 2 of the workload manager 1310 provides an active worklist. When a radiologist selects a worklist, exams within the worklist are displayed in tile format in the second column 2 of the workload manager 1310. Each tile includes metadata that can be useful when a radiologist is determining whether or not he/she is responsible for reading an exam (e.g., the metadata includes an indication of responsible/associated radiologist, patient, exam, referring physician, type, facility, etc.). If necessary or desired, a user can expand a width of the worklist to reveal more patient and exam metadata in each tile.

Several actions can be taken within and/or with respect to a worklist item. Each tile shows a status and available action(s) for the user (e.g., reserve, unreserve, assign, unassign, decline, accept, etc.). In some examples, a right click and/or other selection displays indication(s) of activity by other users on that exam (e.g., viewing, actively dictating, adding images, etc.). Stat or urgent cases can be marked with a red banner at the top left, for example. An exam can be selected from the worklist 4 and provided to the diagnostic hub 1320.

The diagnostic hub 1320 is a home for all of a patient's exam-related information (e.g., non-image data, etc.). The diagnostic hub 1320 positions a radiologist to provide more accurate diagnoses by quickly highlighting relevant comparisons as well as a current patient's broader clinical history. For example, one or more related imaging studies, prior exams, patient history, and/or other clinical documentation can be displayed together with the current exam and/or other clinical scenario under review. In certain examples, file(s) and/or area(s)/portion(s) of files that are relevant can be highlighted for analysis.

The diagnostic hub 1320 includes a patient banner 3. As shown in the example of FIG. 13, the patient banner 3 extends across a top of the diagnostic hub 1320. The patient banner 3 can otherwise be positioned within the diagnostic hub 1320 as well. The patient banner 3 displays patient demographic data as well as other patient information that is persistent and true regardless of the specific exam (e.g., age, medical record number (MRN), cumulative radiation dose, etc.).

The diagnostic hub 1320 also includes a primary exam preview panel 4. The primary exam preview panel 4 provides a summary of the exam that the radiologist is currently responsible for reading (e.g., the exam that was selected from the worklist 2). As shown in the example of FIG. 13, the preview panel 4 is positioned below the patient banner 3 to help keep the radiologist focused on a current task. However, the preview panel 4 can be otherwise positioned in the diagnostic hub 1320. Exam description and reason for exam can be displayed to identify the exam, followed by metadata such as exam time, location, referrer, technologist, etc.

A patient library 5 is devoted to helping a radiologist focus on relevant comparison exams, as well as any additional clinical content to aid in diagnosis. The patient library 5 of the diagnostic hub 1320 includes subsection such as a clinical journey 5a, comparison list 5b, a comparison exam preview panel 5c, etc. The clinical journey 5a is a full patient 'timeline' of imaging exams, as well as other clinical data such as surgical and pathology reports, labs, medications, etc. The longitudinal view of the clinical journey 5a helps the radiologist notice broader clinical patterns more quickly, as well as understand a patient's broader context that may not be immediately evident in a provided reason for the primary exam. Tools can be provided to navigate within the clinical journey 5a. A user can adjust a time frame, filter for specific criteria, turn relevancy on or off, add or remove content categories, etc. The clinical journey 5a also integrates with the comparison list 5b. Modifying filter or search criteria in the clinical journey 5a can impact the exams displayed on the comparison list 5b.

The comparison list 5b is a vertical list of tiles, similar to the worklist 2, displaying available comparison exams for the current patient/primary exam. The comparison list 5b provides a quick access point for selecting comparisons, as opposed to the more longitudinal clinical journey 5a. Display can be limited to only show relevant exams by default, for example.

The comparison exam preview panel 5c is similar to the primary exam preview panel 4, with slight alterations in content display to account for a radiologist's shift in priorities when looking at a comparison (e.g., selected from the comparison list 5b, etc.). Rather than providing a reason for exam, a history and impression from the exam's report are displayed (or the whole report, if extraction is not possible or desired, etc.). The comparison previous panel 5c also generates and/or provides a relevancy score (e.g., 0-100%) based on body part, modality, exam time, and/or other variable(s), if available.

Figure 14:
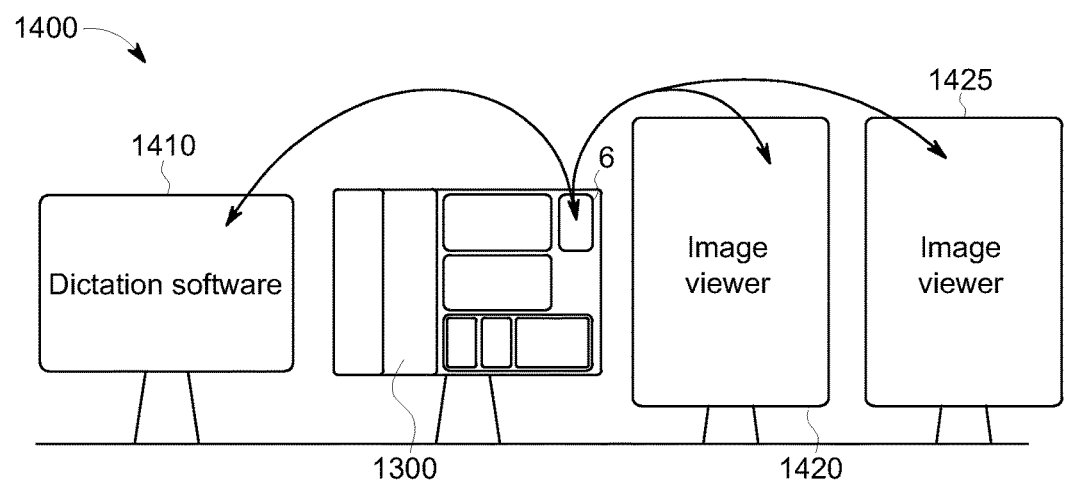
FIG. 14 illustrates an example system in which a bridge enables radiologists to easily navigate back and forth between a radiology desktop, image viewer(s), and dictation software, while maintaining patient context.

The diagnostic hub 1320 can also include an image viewer/dictation software bridge 6. As illustrated in the example of FIG. 14, the bridge 6 enables radiologists to easily navigate back and forth between the radiology desktop 1300, image viewer 1420, 1425, and dictation software 1410, while maintaining patient context. Using the bridge 6, a radiologist's complete end-to-end workflow can be supported.

Figure 15:
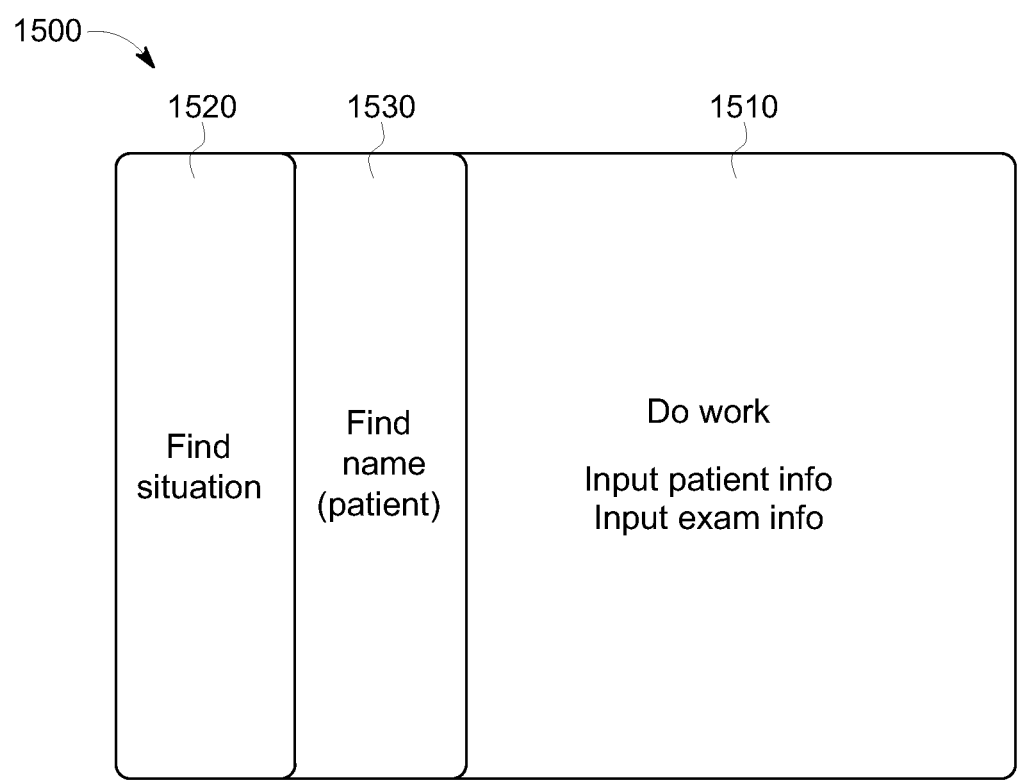
FIG. 15 illustrates an example technologist desktop.

In certain examples, a left-to-right, drill down model can be applied to roles other than a radiologist (other -ologies than radiology). FIG. 15 illustrates an example technologist desktop 1500. The example technologist desktop interface 1500 includes a work area 1510 to input patient and exam information. The example interface 1500 also includes a clinical situation finder 1520 and a patient finder 1530. Similar to the workflow described above, a user can search for a clinical situation via the situation finder 1520, search for a name related to the situation via the name or patient finder 1530, and work with respect to the identified patient and clinical situation via workspace 1510. At each stage, information associated with the selection is dynamically retrieved and/or updated from an external source (e.g., a clinical data server, etc.) and dynamically rendered via the interface 1500. The configuration of the interfaced 1500 unfolds or expands into multiple columns and/or other sections based on selected option(s) and retrieved information, for example.

VI. EXAMPLE INTERACTION FRAMEWORK METHODS

Figure 16:
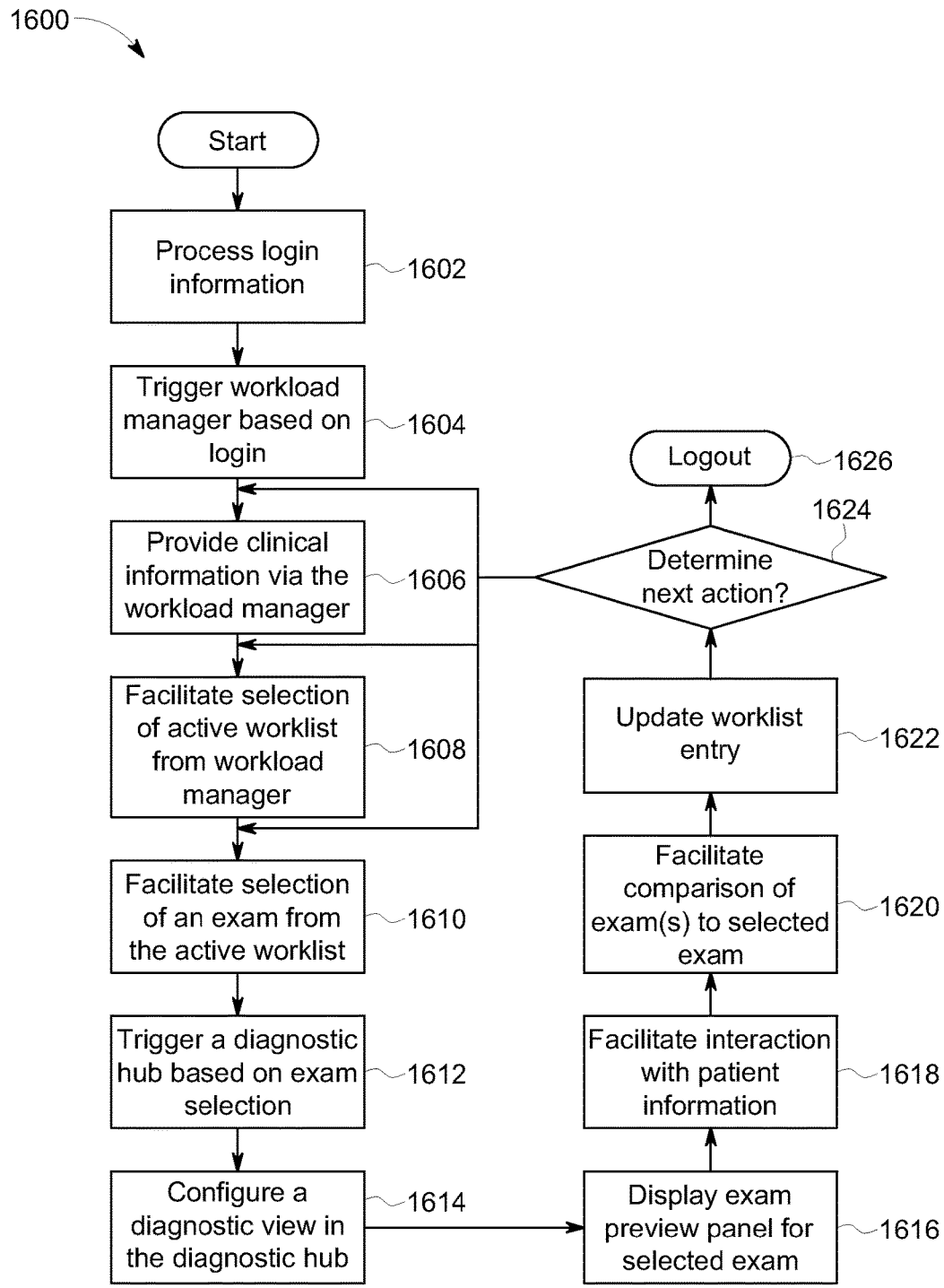
FIG. 16 illustrates a flow diagram for an example method to integrate a worklist with a diagnostic workspace via an interaction framework.

Flowcharts representative of example machine readable instructions for implementing and/or executing in conjunction with the example systems and interfaces of FIGS. 11-15 are shown in FIG. 16. In these examples, the machine readable instructions comprise a program for execution by a processor such as the processor 2012 shown in the example processor platform 2000 discussed below in connection with FIG. 20. The program can be embodied in software stored on a tangible computer readable storage medium such as a CD-ROM, a floppy disk, a hard drive, a digital versatile disk (DVD), a BLU-RAY™ disk, or a memory associated with the processor 2012, but the entire program and/or parts thereof could alternatively be executed by a device other than the processor 2012 and/or embodied in firmware or dedicated hardware. Further, although the example program is described with reference to the flowchart illustrated in FIG. 16, many other methods of implementing the examples disclosed and described here can alternatively be used. For example, the order of execution of the blocks can be changed, and/or some of the blocks described can be changed, eliminated, or combined.

As mentioned above, the example processes of FIG. 16 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 16 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 16 illustrates a flow diagram for an example method 1600 to integrate a worklist with a diagnostic workspace via an interaction framework. At block 1602, a login is processed to access the interaction framework. For example, a user provides information for single sign on (SSO) to a system including the interaction framework. At block 1604, based on the login, a workload manager (WM) is triggered. The WM is displayed via a graphical user interface on a display screen, for example. At block 1606, information, such as a plurality of worklists and perhaps a plurality of patients associated with the worklist(s), is provided via the WM.

At block 1608, selection of an active worklist from the WM is facilitated. The active worklist is displayed via the WM. At block 1610, selection of an exam from the active worklist is facilitated. For example, the active worklist displays a list of available exams associated with the active worklist, and one of the list of exams is selected.

At block 1612, a diagnostic hub (DH) is triggered based on selection of the exam. At block 1614, a diagnostic view is configured in the diagnostic hub for the selected exam according to the worklist and patient information. For example, the graphical user interface of the display screen adjusts the configuration such that the DH is displayed adjacent to the WM in the graphical user interface. A patient banner can be provided in conjunction with the selected exam via the DH diagnostic view. The patient banner provides certain summary, demographic, and/or other identifying information for a patient associated with the selected exam.

At block 1616, an exam preview panel is displayed based on the selected exam and patient. The exam preview panel provides a summary of the selected exam that the radiologist is currently responsible for reading, for example.

At block 1618, interaction with patient information is facilitated via the diagnostic view or workspace of the DH. Patient information can be viewed, reviewed, modified, added, deleted, etc., via the DH. At block 1620, one or more exams are chosen for comparison to the primary selected exam displayed via the preview panel. For example, a patient library provided via the DH provides relevant comparison exam(s) and/or other clinical content to aid in diagnosis.

At block 1622, a patient record and associated exam worklist entry can be updated based on the comparison. Thus, imaging-related clinical context, image review/comparison, and/or other clinical and/or operational insight can be factored into a report and/or other analysis of the exam. The report and/or other analysis can be saved in conjunction with the patient, exam, and/or worklist, for example.

At block 1624, after the update, a user can choose to branch to a variety of next actions. For example, control can switch to block 1606 with updated clinical information provided via the workload manager. Alternatively or in addition, control can shift to block 1608 for selection of another active worklist from the workload manager. As another option, control can shift to block 1610 for selection of another exam from the current active worklist. Alternatively, at block 1626, logout is facilitated.

Thus, via a graphical user interface can be configured to dynamically accommodate both a DH and WM and facilitate workload management as well as communication and collaboration among healthcare practitioners.

VII. EXAMPLE PATIENT LIBRARY SYSTEMS AND ASSOCIATED METHODS

Figure 17:
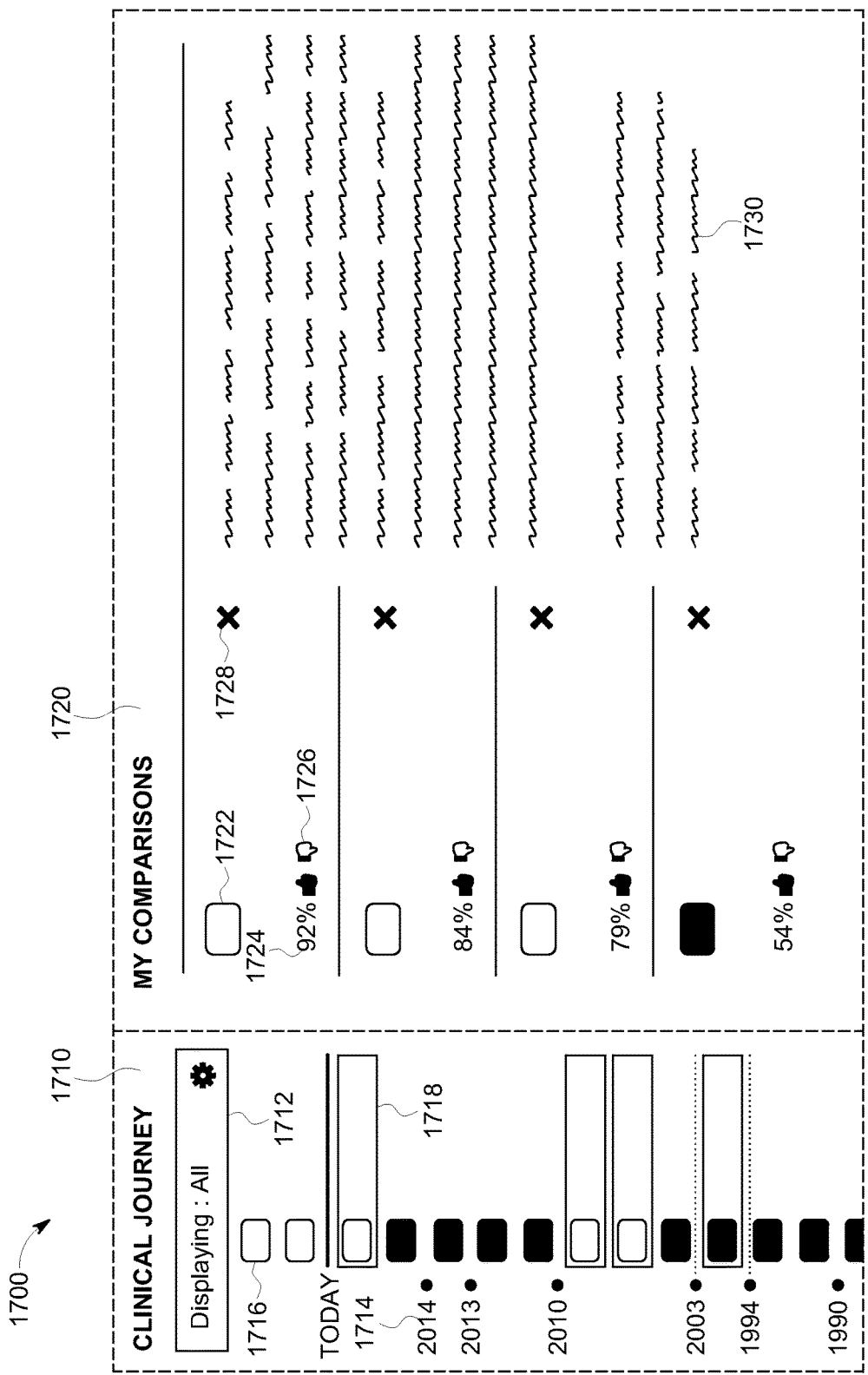
FIG. 17 illustrates an example Patient Library providing a patient history or timeline area, an information comparison area, and a more detailed comparison preview panel.

FIG. 17 illustrates an example Patient Library 1700 providing a patient history or timeline area 1710 (e.g., referred to as "Clinical Journey"), an information comparison area 1720 (e.g., referred to as "My Comparisons"), and a more detailed comparison preview panel 1730 (e.g., referred to as "Comparison Exam Preview Panel").

In the example of FIG. 17, the Clinical Journey 1710 is a full patient 'timeline' of imaging exams, as well as other clinical data such as surgical and pathology reports, labs, meds, etc. The longitudinal view provided by the clinical journey 1710 helps a radiologist and/or other user notice clinical patterns more quickly and understand a patient's broader context that may not be immediately evident in a provided reason for a primary exam (e.g., a given clinical scenario). The clinical journey 1710 provides a more comprehensive collection of events and information for access and review if suggestions provided by the IRCC Relevancy Algorithm are not sufficient to aid the radiologist in his or her diagnosis, for example.

In certain examples, tools are provided to modify a type and/or range of data displayed within the Clinical Journey 1710. For example, the user can adjust a time frame, filter for specific criteria, turn relevancy on or off, add or remove content categories (e.g., for documentation beyond imaging exams), etc.

As shown in the example of FIG. 17, the clinical journey 1710 includes a display filter 1712 allowing display of some, all, a particular type/category, etc., of event and/or date in the clinical journey 1710 view. The clinical journey 1710 view also includes a plurality of date indicators 1714, a document/event indicator 1716, and a further detail box 1718 associated with at least some events 1716 on the timeline or journey 1710.

As illustrated in the example of FIG. 17, the My Comparisons 1720 is a list of comparison(s) that a user, such as a radiologist, can use to inform his or her read of an exam. When a radiologist opens an exam off of his or her worklist, "My Comparisons" 1720 is auto-populated with a select few comparison items from the patient's history that the Relevancy Algorithm calculated to be most relevant to the exam that the radiologist is reading. The Relevancy Algorithm uses a combination of machine learning, natural language processing (NLP), and data usage information to determine not only the relevant comparisons, but specific information (e.g., keywords, phrases, other media, etc.) within the comparison content that is likely to be valuable.

The "My Comparisons" list 1720 is not immutable. Items can be added and removed from the list 1720 as the radiologist reads the current exam and determines that suggested comparison(s) do not contain valuable information, and/or that other available content would/could be more informative.

As shown in the example of FIG. 17, the list of comparison 1720 includes a one or more comparison item indicators 1722. Each item 1722 includes a preference/relevancy indicator 1724 and a feedback mechanism 1726. A user can provide his or her feedback regarding a particular item 1722 via the feedback mechanism 1726 (e.g., thumbs up/thumbs down, star rating, alphanumeric rating, plus/minus, etc.), and a compilation of feedback ratings 1724 is provided in conjunction with the item 1722. Thus, as shown in the example of FIG. 17, 92% of users found the first item relevant and/or otherwise useful to their clinical scenario, while 84% found the second item relevant. If a user wishes to remove an item 1722 from the my comparisons list 1720, an option 1728 is provided for the user to do so.

As shown in the example of FIG. 17, the Comparison Exam Preview Panel 1730 is a simple viewing window that allows the radiologist to open a relevant comparison from either of the other two components 1710, 1720 to inspect and consume its contents. Contents of the preview panel 1730 are determined by a type of comparison content provided by components 1710, 1720, but can be any information from structured/unstructured text to image to video or any combination thereof, for example.

Within the Comparison Exam Preview Panel 1730, the radiologist can view either entire contents of a selected comparison or only piece(s) that were identified and used by the relevancy algorithm in its relevancy calculation.

The Patient Library interface 1700 is designed so that a radiologist and/or other user can easily sort and group helpful information in a single location for reference at any point during his or her workflow (e.g., during a radiologist's dictation, etc.). The relevancy algorithm populates My Comparisons 1720 with suggested content, and as the radiologist and/or other user moves additional items from the Clinical Journey 1710 into My Comparisons 1720 or rates items already present, criteria about those comparisons is input back to the relevancy algorithm.

Additionally, the radiologist can choose at any time to rate the comparisons on the My Comparisons list 1720 via a rating or scoring such as a simple 'thumbs up/down' system, star-based rating or scoring system, alphanumeric scoring system, etc. For example, in a thumbs up/thumbs down scale, a thumbs up increases a weighting of that exam's criteria in the relevancy algorithm for subsequent exams, while a thumbs down removes the comparison from My Comparisons 1720 and decreases the criteria weighting by the relevancy algorithm.

Figure 18A:
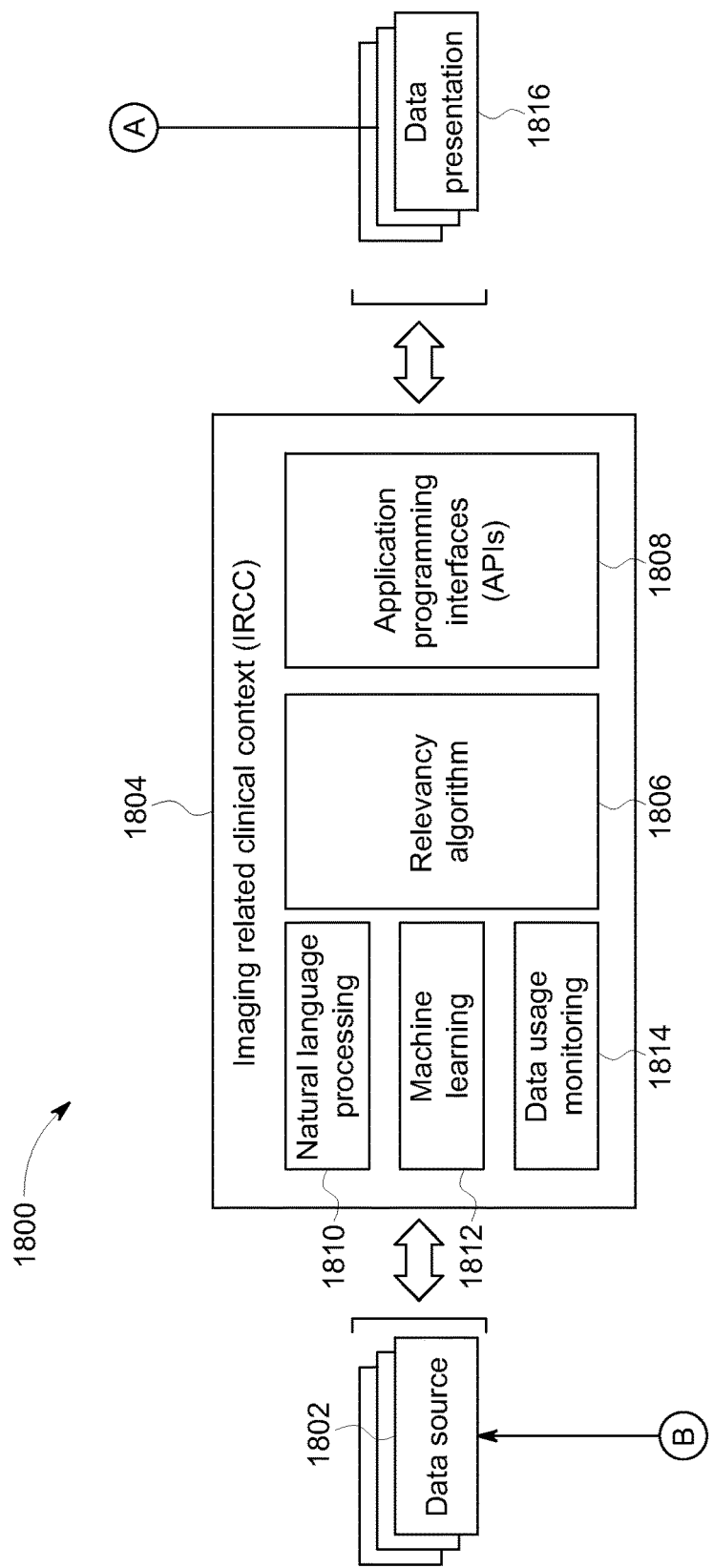
FIG. 18 illustrates an example system including a feedback loop between actions taken on a patient library interface and a clinical context processor providing a relevancy algorithm.
Figure 18B:
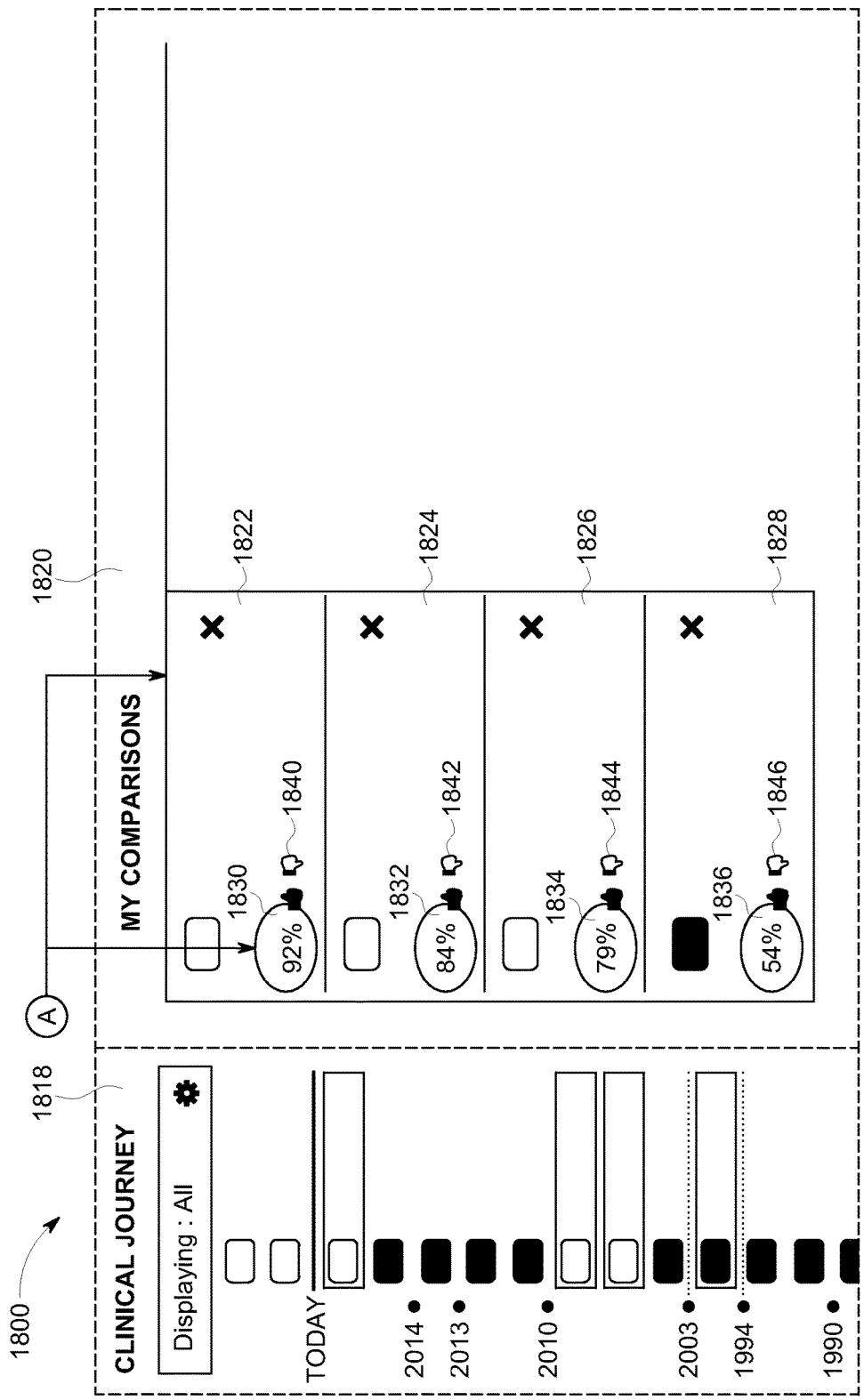
Figure 18C:
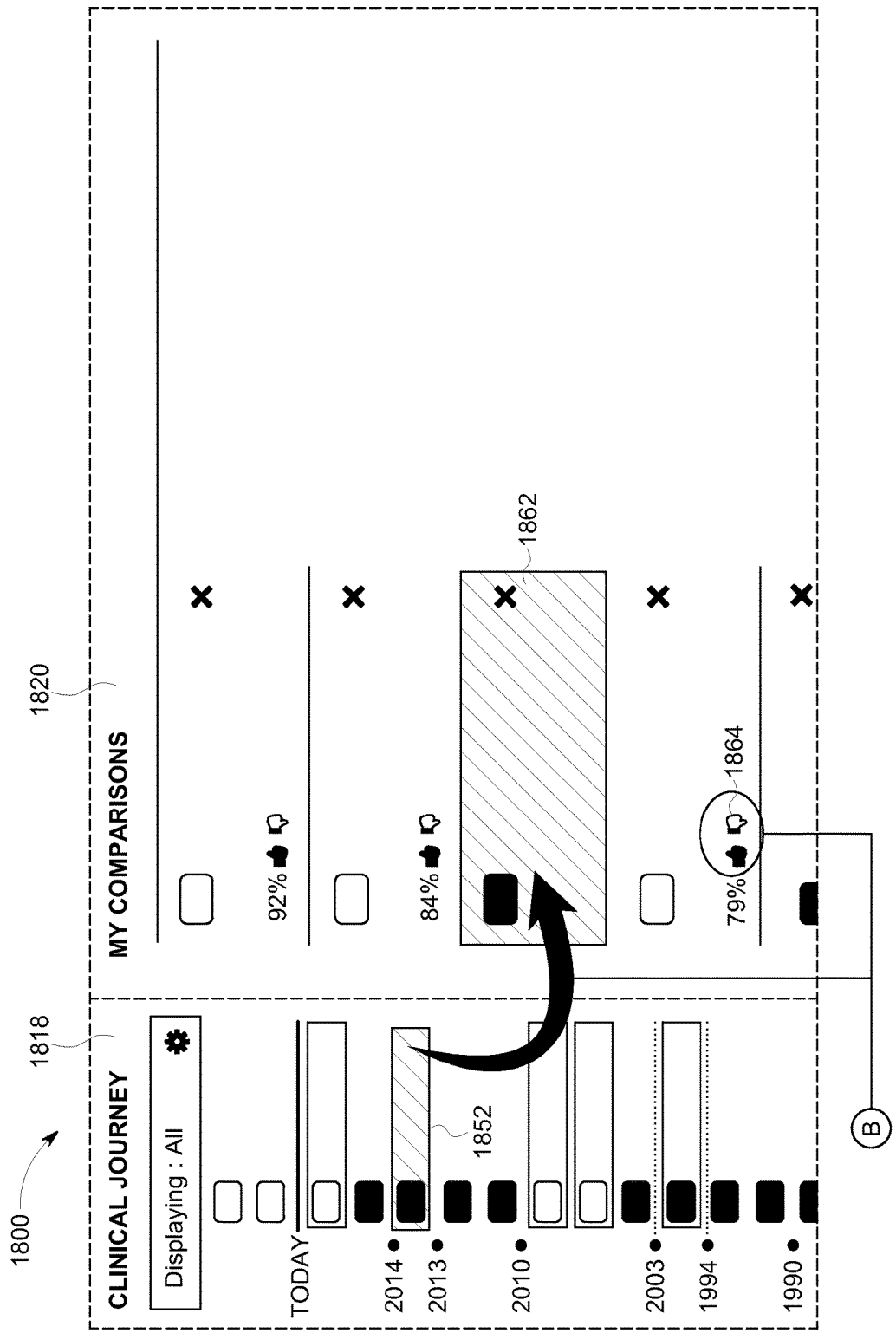

FIG. 18 illustrates an example system 1800 including a feedback loop between actions taken on a patient library interface and an IRCC processor providing a relevancy algorithm. As shown in the example of FIG. 18, an IRCC processor 1804 processes document(s) and/or other content from data source(s) 1802 and provides output data for presentation 1816. Similar to FIG. 4, described above, the processor 1804 applies NLP, machine learning, and data usage monitoring in conjunction with a relevancy algorithm and makes output data 1816 available via one or more APIs.

For example, output data 1816 deemed to be relevant to a particular clinical scenario by the IRCC processor 1804 is provided to a user's clinical journey 1818 and comparisons 1820 lists. As shown in the example of FIG. 18, data output 1816 can provided to the my comparison lists 1820 as items 1822, 1824, 1826, 1828. An indication of preference/relevancy rating 1830, 1832, 1834, 1836 is provided in conjunction with each item 1822, 1824, 1826, 1828, and a user can provide his or her own feedback 1840, 1842, 1844, 1846 with respect to each item 1822, 1824, 1826, 1828 for the particular clinical scenario which the user is currently reviewing.

Additionally, as shown in the example of FIG. 18, a user can add (e.g., by selecting, drag-and-drop, etc.) an entry 1852 from the clinical journey 1818 to the comparison list 1820. The new comparison entry 1862 is viewable in comparison to a current exam and/or other document under review by the user, for example. Further, when the user provides a relevancy or other feedback rating 1864, the feedback is stored at the data source 1802 and is provided in subsequent analysis by the IRCC processor 1804 to generate relevant output data 1816.

Figure 19:
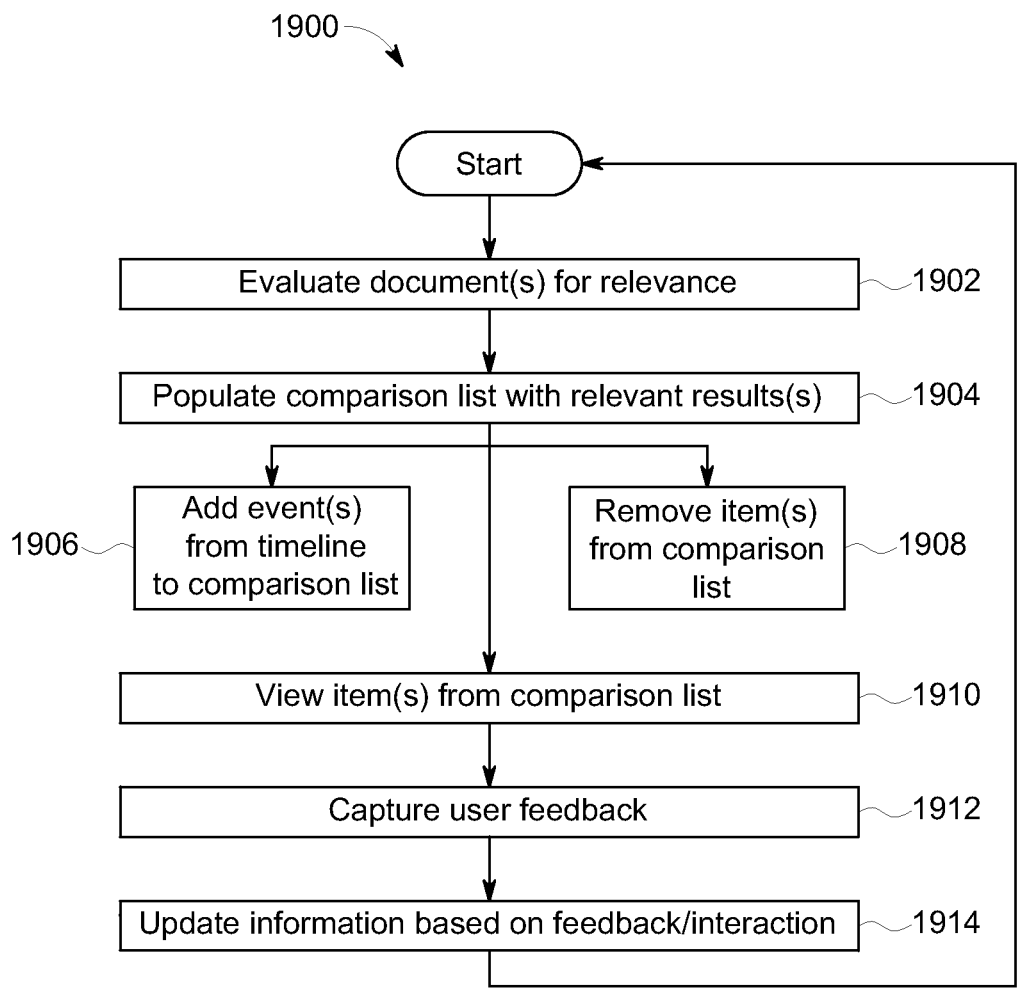
FIG. 19 illustrates a flow diagram for an example method to present comparison information and gather feedback for a clinical scenario.

Flowcharts representative of example machine readable instructions for implementing and/or executing in conjunction with the example systems, algorithms, and interfaces of FIGS. 17-18 are shown in FIG. 19. In these examples, the machine readable instructions comprise a program for execution by a processor such as the processor 2012 shown in the example processor platform 2000 discussed below in connection with FIG. 20. The program can be embodied in software stored on a tangible computer readable storage medium such as a CD-ROM, a floppy disk, a hard drive, a digital versatile disk (DVD), a BLU-RAY™ disk, or a memory associated with the processor 2012, but the entire program and/or parts thereof could alternatively be executed by a device other than the processor 2012 and/or embodied in firmware or dedicated hardware. Further, although the example program is described with reference to the flowchart illustrated in FIG. 19, many other methods of implementing the examples disclosed and described here can alternatively be used. For example, the order of execution of the blocks can be changed, and/or some of the blocks described can be changed, eliminated, or combined.

As mentioned above, the example processes of FIG. 19 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 19 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 19 illustrates a flow diagram for an example method 1900 to present comparison information and gather feedback for a clinical scenario. At block 1902, one or more documents are evaluated for relevance with respect to a clinical scenario. For example, prior image studies are evaluated with respect to a current head CT exam being read by a radiologist. Relevancy and/or other importance can be evaluated and determined using a relevancy algorithm, for example. The relevancy algorithm can take into account aspect(s) of the document(s) themselves, characteristic(s) of the current clinical scenario, and/or preference/rating information regarding the document(s), for example, to provide some or all of the source document(s) for comparison in review of the clinical scenario. Evaluation can be triggered based on input and/or selection of a clinical scenario, addition of new and/or updated information at the data source, etc.

At block 1904, relevant result(s) populate a list of comparison items for review. For example, indicators (e.g., thumbnails, icons, titles, summaries, and/or other representation, etc.) of one or more items (e.g., images, reports, and/or other documents, etc.) evaluated and determined to be relevant and/or otherwise useful for the given clinical scenario are provide from the IRCC processor to the list of comparison items in the patient library on a radiologist graphical user interface.

At block 1906, one or more events from a timeline can be added to list of comparisons for review. For example, a patient timeline and/or other list of items/events related to the patient can be displayed in conjunction with the list of comparison items via the patient library, and one or more of the patient timeline items can be added to the list of items for comparison with the clinical scenario.

In certain examples, an item provided in the list of items for comparison from the relevancy algorithm can also be added to the clinical journey or patient timeline. Thus, the algorithm may identify a patient event that should be but wasn't previously in the timeline, and the interface can allow the event to be added to the timeline.

At block 1908, one or more items can be removed from the list of comparisons for review. For example, a user can drag, click, etc., to remove an item from the list so that the removed item is no longer included for comparison with respect to the clinical scenario.

At block 1910, one or more items from the list of comparisons can be viewed in conjunction with one or more items associated with the clinical scenario. For example, one or more items remaining in the comparison list can be displayed via a preview panel, comparison screen, reading window, etc., in conjunction with the current clinical scenario. For example, a current exam can be compared by a radiologist to one or more prior imaging studies, lab results, examination notes, etc., for the same patient and/or similar clinical scenario.

At block 1912, user feedback is captured with respect to one or more items in the list of comparison items. For example, the user can rate the relevance and/or other usefulness of one or more items in the comparison list. If an item was relevant/useful, the user can give the item a "thumbs up" and/or other positive rating. If an item was not relevant/useful, the user can give the item a "thumbs down" and/or other negative rating. In certain examples, the rating may be a more granular rating rather than a binary positive/negative evaluation.

At block 1914, information is updated at the data source based on feedback and/or other interaction. For example, user feedback, added/removed item(s) from the comparison list, new report(s), etc., can be provided to the data source, which can, in turn, trigger further analysis by the relevancy algorithm and the IRCC processor.

VIII. COMPUTING DEVICE

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein can include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and can include volatile and non-volatile, removable and non-removable media for storage of electronic-formatted information such as computer readable program instructions or modules of instructions, data, etc. that may be stand-alone or as part of a computing device. Examples of computer readable storage medium or computer program products can include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein can include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 20:
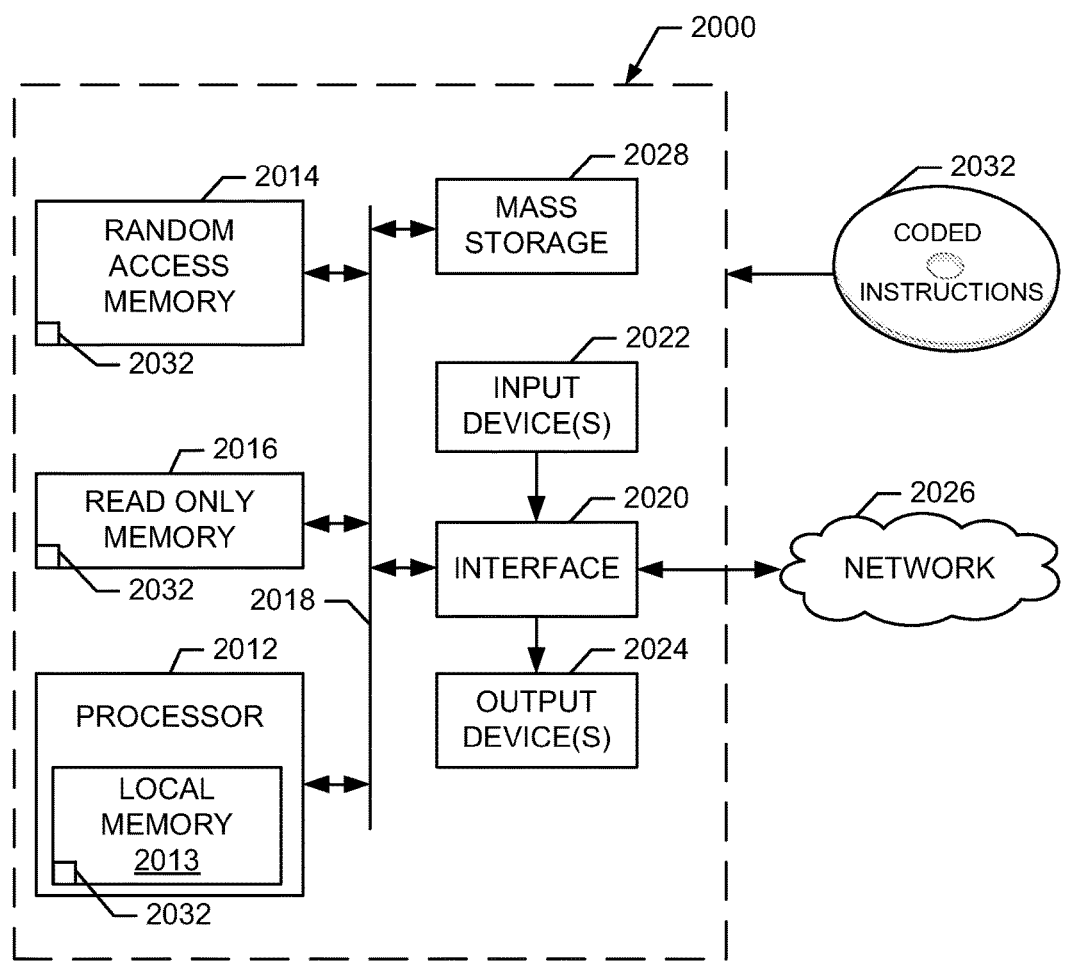
FIG. 20 shows a block diagram of an example processor system that can be used to implement systems and methods described herein.

FIG. 20 is a block diagram of an example processor platform 2000 capable of executing instructions to implement the example systems and methods disclosed and described herein. The processor platform 2000 can be, for example, a server, a personal computer, a mobile device (e.g., a cell phone, a smart phone, a tablet such as an IPAD™), a personal digital assistant (PDA), an Internet appliance, or any other type of computing device.

The processor platform 2000 of the illustrated example includes a processor 2012. The processor 2012 of the illustrated example is hardware. For example, the processor 2012 can be implemented by one or more integrated circuits, logic circuits, microprocessors or controllers from any desired family or manufacturer.

The processor 2012 of the illustrated example includes a local memory 2013 (e.g., a cache). The processor 2012 of the illustrated example is in communication with a main memory including a volatile memory 2014 and a non-volatile memory 2016 via a bus 2018. The volatile memory 2014 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2016 can be implemented by flash memory and/or any other desired type of memory device. Access to the main memory 2014, 2016 is controlled by a memory controller.

The processor platform 2000 of the illustrated example also includes an interface circuit 2020. The interface circuit 2020 can be implemented by any type of interface standard, such as an Ethernet interface, a universal serial bus (USB), and/or a PCI express interface.

In the illustrated example, one or more input devices 2022 are connected to the interface circuit 2020. The input device(s) 2022 permit(s) a user to enter data and commands into the processor 2012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 2024 are also connected to the interface circuit 2020 of the illustrated example. The output devices 2024 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 2020 of the illustrated example, thus, typically includes a graphics driver card, a graphics driver chip or a graphics driver processor.

The interface circuit 2020 of the illustrated example also includes a communication device such as a transmitter, a receiver, a transceiver, a modem and/or network interface card to facilitate exchange of data with external machines (e.g., computing devices of any kind) via a network 2026 (e.g., an Ethernet connection, a digital subscriber line (DSL), a telephone line, coaxial cable, a cellular telephone system, etc.).

The processor platform 2000 of the illustrated example also includes one or more mass storage devices 2028 for storing software and/or data. Examples of such mass storage devices 2028 include floppy disk drives, hard drive disks, compact disk drives, Blu-ray disk drives, RAID systems, and digital versatile disk (DVD) drives.

The coded instructions 2032 can be stored in the mass storage device 2028, in the volatile memory 2014, in the non-volatile memory 2016, and/or on a removable tangible computer readable storage medium such as a CD or DVD.

VI. CONCLUSION

Thus, certain examples provide systems and methods to organize, compare, customize, and evaluate clinical documents and/or other clinical data with respect to a current clinical situation or scenario. Whereas, with prior systems, a radiologist is presented with an incomplete assessment at the beginning of an imaging study read and typically has no ability to change his or her workspace or rid themselves of comparisons that he or she judges to ultimately be unhelpful, certain examples allow the radiologist to dynamically customize his or her workspace and continuously adapt information available for comparison.

Furthermore, prior workflows lack an ability for 'place saving' when a radiologist is looking at a longitudinal view of a patient's comparison imaging history and/or tracking content that the user has already visited. By combining a longitudinal Clinical Journey view with an additional collection space (e.g., a My Comparisons list), a radiologist is enabled to assemble helpful information and keep it front and center for continual access.

As a result, reading time for imaging exams is decreased because the radiologist does not have to spend as much time searching for appropriate comparisons and potentially re-locating the comparison information if returning more than once to the information. In certain examples, a vertical layout improves navigation by matching with standard mouse behaviors (e.g., wheel scrolling) and allowing more comparison items to be shown in a single view than when the same data is organized horizontally, as in a standard 'timeline' view.

In certain examples, capturing feedback through actions taken by a user, such as a radiologist, etc., (e.g., by adding/subtracting exams, associated documentation, etc.), increases a likelihood that the user will contribute feedback and improve the accuracy of the relevancy algorithm.

Additionally, a consolidated view of multiple types of clinical content decreases a need for third party applications such as electronic health records (EHRs) that are non-specific to imaging. This de-clutters user workspace and increases efficiency.

Rather than simple terminology matching, relevancy is determined based on a greater granularity of clinical content, usage patterns of the same and/or similar users over time, as well as other types of comparison content (e.g., clinical notes, other -ology imaging, patient-centric communication, etc.).

In certain examples, feedback provided by one radiologist provides improved suggestions not just to the individual, but to eventually to entire departments or enterprises. In certain examples, a Patient Library builds a single packet of comparison data that is useful in the context of a radiologist's current activity. Switching to a different activity (e.g., a different type of exam, a different task for that exam, etc.) switches a type of content provided and gathered. An item in "My Comparisons" ultimately becomes relevant not only to the exam being read, but to the other content on the "My Comparisons" list. Creating these collections strengthens ontological relationships between medical events at a more holistic level because of the granularity of the data analyzed.

Certain examples provide a bird's eye view that allows the radiologist to view everything, regardless of relevancy or other filtering criteria. This bird's eye view (e.g., the Clinical Journey) sits side by side with the collection space so that a user can quickly compare 'what they have right now' with 'what they could have', for example.

Certain examples provide an event-based architecture generating more efficient data processing. In certain examples, natural language processing creates an easy to understand information hierarchy. In certain examples, an adaptable system can respond to multiple clinical environments. Faster display of information can lead to more efficient workflow.

Certain examples provide general schema that can be ported to a variety of databases. Certain examples further provide a user-friendly wizard to create worklist definitions. Worklist definitions can be ported among schema. Certain examples leverage an entity framework to provide functionality, collaboration, modules, and metadata management in an entity framework, for example. Worklists can be dynamically built and dynamically injected with context and user session information, for example.

Thus, certain examples provide a diagnostic cockpit that aggregates clinical data and artifacts. Certain examples facilitate determination of data relevancy factoring in patient, user, and study context. Certain examples provide diagnostic decision support through the integrated diagnostic cockpit.

Certain examples provide a dynamically adjustable interaction framework including both a workload manager and diagnostic hub accommodating a variety of worklists, exams, patients, comparisons, and outcomes. Certain examples improve operation of a graphical user interface and associated display and computer/processor through adaptive scalability, organization, and correlation.

Certain examples provide a clinical knowledge platform that enables healthcare institutions to improve performance, reduce cost, touch more people, and deliver better quality globally. In certain examples, the clinical knowledge platform enables healthcare delivery organizations to improve performance against their quality targets, resulting in better patient care at a low, appropriate cost. Certain examples facilitate improved control over data. For example, certain example systems and methods enable care providers to access, view, manage, and manipulate a variety of data while streamlining workload management. Certain examples facilitate improved control over process. For example, certain example systems and methods provide improved visibility, control, flexibility, and management over workflow. Certain examples facilitate improved control over outcomes. For example, certain example systems and methods provide coordinated viewing, analysis, and reporting to drive more coordinated outcomes.

Certain examples leverage information technology infrastructure to standardize and centralize data across an organization. In certain examples, this includes accessing multiple systems from a single location, while allowing greater data consistency across the systems and users.

Technical effects of the subject matter described above can include, but are not limited to, providing systems and methods to enable an interaction and behavior framework to determine relevancy and recommend information for a given clinical scenario. Clinical workflow and analysis are dynamically driven based on available information, user preference, display configuration, etc. Moreover, the systems and methods of this subject matter described herein can be configured to provide an ability to better understand large volumes of data generated by devices across diverse locations, in a manner that allows such data to be more easily exchanged, sorted, analyzed, acted upon, and learned from to achieve more strategic decision-making, more value from technology spend, improved quality and compliance in delivery of services, better customer or business outcomes, and optimization of operational efficiencies in productivity, maintenance and management of assets (e.g., devices and personnel) within complex workflow environments that may involve resource constraints across diverse locations.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising:
a processor configured to generate and display a graphical user interface defining a first display area for interaction including at least:
a diagnostic hub and a workload manager in the first display area,
the workload manager to display a worklist of exams, the workload manager to close and transform to a miniaturized form in the first display area when the worklist is not in use, the diagnostic hub to expand to occupy a remainder of the first display area when the workload manager is in the miniaturized form and to reduce to accommodate the workload manager when the worklist is in use,
the diagnostic hub to display, in the first display area via the graphical user interface when triggered by selection of an exam from a worklist, at least:
an exam preview panel to preview the selected exam; and
a patient library interface to display, when accessed via the exam preview panel, a plurality of events along a timeline for a patient and a list of items for comparison to a clinical scenario including a reason for the selected exam, the clinical scenario specified in a configuration of the patient library interface to trigger collection of the list of items for comparison, the processor to receive and add items to the list of items for comparison based on a relevancy analysis of each item to the clinical scenario, the relevancy analysis to include a relevancy algorithm including a combination of machine learning, natural language processing, and data usage information applied to each item based on the selected exam and the reason for the selected exam to calculate a relevancy score for the respective item and to build the list of items ranked by their respective relevancy score for comparison in association with the clinical scenario, the processor to facilitate user feedback to add, remove, and rate relevance of one or more items in the list of items for comparison, the processor to display one or more items from the list of items for comparison in conjunction with documentation from the clinical scenario and to facilitate user interaction with the one or more items and documentation, the processor to update a data source based on the user feedback and user interaction.

2. The system of claim 1, wherein the updating based on the user feedback and user interaction adjusts the relevancy algorithm applied to subsequent items and clinical scenario.

3. The system of claim 1, further comprising a data relevancy processor configured to process a data event provided by a data source by applying natural language processing and machine learning to the data event based on the clinical scenario and to determine relevancy of the data event with respect to the clinical scenario based on a combination of domain knowledge and user knowledge to filter and determine relevancy of the data event with respect to the clinical scenario, the data relevancy processor to output the data event to the list of items for comparison based on the determined relevancy to the clinical scenario.

4. The system of claim 3, wherein the determined relevancy comprises a relevancy score displayed with the data event in the list of items for comparison.

5. The system of claim 1, wherein the add and remove of an item to the list of items for comparison further comprises at least one of selecting and dragging and dropping an item from one of the timeline and the list of items for comparison to the other of the timeline and the list of items for comparison.

6. The system of claim 1, wherein the timeline and the list of items for comparison are provided via the patient library interface adjacent to a panel displaying the comparison.

7. The system of claim 1, wherein the clinical scenario comprises an imaging exam and one or more of the list of items for comparison comprise one or more prior imaging studies.

8. The system of claim 1, wherein the diagnostic hub further includes a bridge to tie the diagnostic hub to an image viewer and dictation software, the bridge to enable navigation between the diagnostic hub, the image viewer, and the dictation software while maintaining a patient context across the diagnostic hub, the image viewer, and the dictation software.

9. A computer-implemented method comprising:
monitoring and managing, using a processor, a graphical user interface defining a first display area for interaction including at least a diagnostic hub and a workload manager, the workload manager to display a worklist of exams, the workload manager to close and transform to a miniaturized form in the first display area when the worklist is not in use, the diagnostic hub to expand to occupy a remainder of the first display area when the workload manager is in the miniaturized form and to reduce to accommodate the workload manager when the worklist is in use, the diagnostic hub to display, in the first display area when triggered by selection of an exam from a worklist, at least an exam preview panel and a patient library interface;
receiving, using the processor, one or more data events determined to be relevant to a clinical scenario including a reason for an exam, the clinical scenario specified in a configuration of the patient library interface to trigger collection of the list of items for comparison, the patient library interface accessible via an exam preview panel triggered by selection of the exam from the worklist;
displaying, via the patient library interface, a plurality of events along a timeline for a patient and a list of items for comparison to the clinical scenario based on the clinical scenario and the one or more data events;
receiving and adding, using the processor, items to the list of items for comparison based on a relevancy analysis of each item to the clinical scenario, the relevancy analysis to include a relevancy algorithm including a combination of machine learning, natural language processing, and data usage information applied to each item based on the selected exam and the reason for the selected exam to calculate a relevancy score for the respective item and to build the list of items ranked by their respective relevancy score for comparison in association with the clinical scenario;
facilitating, using the processor, user feedback to add, remove, and rate relevance of one or more items in the list of items for comparison;
displaying, using the processor, one or more items from the list of items for comparison in conjunction with documentation from the clinical scenario;
facilitating, using the processor, user interaction with the one or more items and documentation; and
updating, using the processor, a data source based on the user feedback and user interaction.

10. The method of claim 9, wherein the updating based on the user feedback and user interaction adjusts the relevancy algorithm applied to subsequent items and clinical scenario.

11. The method of claim 9, further comprising processing a data event provided by a data source by applying natural language processing and machine learning to the data event based on the clinical scenario and to determine relevancy of the data event with respect to the clinical scenario based on a combination of domain knowledge and user knowledge to filter and determine relevancy of the data event with respect to the clinical scenario; and outputting the data event to the list of items for comparison based on the determined relevancy to the clinical scenario.

12. The method of claim 11, wherein the determined relevancy comprises a relevancy score displayed with the data event in the list of items for comparison.

13. The method of claim 9, wherein the add and remove of an item to the list of items for comparison further comprises at least one of selecting and dragging and dropping an item from one of the timeline and the list of items for comparison to the other of the timeline and the list of items for comparison.

14. The method of claim 9, wherein the timeline and the list of items for comparison are provided via the patient library interface adjacent to a panel displaying the comparison.

15. The method of claim 9, wherein the clinical scenario comprises an imaging exam and one or more of the list of items for comparison comprise one or more prior imaging studies.

16. A computer-readable storage medium including program instructions for execution by a computing device, the instructions, when executed, causing the computing device to execute a method, the method comprising:
monitoring and managing a graphical user interface defining a first display area for interaction including at least a diagnostic hub and a workload manager, the workload manager to display a worklist of exams, the workload manager to close and transform to a miniaturized form in the first display area when the worklist is not in use, the diagnostic hub to expand to occupy a remainder of the first display area when the workload manager is in the miniaturized form and to reduce to accommodate the workload manager when the worklist is in use, the diagnostic hub to display, in the first display area when triggered by selection of an exam from a worklist, at least an exam preview panel and a patient library interface;

receiving one or more data events determined to be relevant to a clinical scenario including a reason for an exam, the clinical scenario specified in a configuration of the patient library interface to trigger collection of the list of items for comparison, the patient library interface accessible via an exam preview panel triggered by selection of the exam from the worklist;

displaying, via the patient library interface, a plurality of events along a timeline for a patient and a list of items for comparison to the clinical scenario based on the clinical scenario and the one or more data events;

receiving and adding items to the list of items for comparison based on a relevancy analysis of each item to the clinical scenario, the relevancy analysis to include a relevancy algorithm including a combination of machine learning, natural language processing, and data usage information applied to each item based on the selected exam and the reason for the selected exam to calculate a relevancy score for the respective item and to build the list of items ranked by their respective relevancy score for comparison in association with the clinical scenario;

facilitating user feedback to add, remove, and rate relevance of one or more items in the list of items for comparison;

displaying one or more items from the list of items for comparison in conjunction with documentation from the clinical scenario;

facilitating user interaction with the one or more items and documentation; and updating a data source based on the user feedback and user interaction.

17. The computer-readable storage medium of claim 16, wherein the updating based on the user feedback and user interaction adjusts the relevancy algorithm applied to subsequent items and clinical scenario.

18. The computer-readable storage medium of claim 16, wherein the method further comprises processing a data event provided by a data source by applying natural language processing and machine learning to the data event based on the clinical scenario and to determine relevancy of the data event with respect to the clinical scenario based on a combination of domain knowledge and user knowledge to filter and determine relevancy of the data event with respect to the clinical scenario; and outputting the data event to the list of items for comparison based on the determined relevancy to the clinical scenario.

19. The computer-readable storage medium of claim 18, wherein the determined relevancy comprises a relevancy score displayed with the data event in the list of items for comparison.

20. The computer-readable storage medium of claim 16, wherein the add and remove of an item to the list of items for comparison further comprises at least one of selecting and dragging and dropping an item from one of the timeline and the list of items for comparison to the other of the timeline and the list of items for comparison.

21. The computer-readable storage medium of claim 16, wherein the clinical scenario comprises an imaging exam and one or more of the list of items for comparison comprise one or more prior imaging studies.

* * * * *